(12) United States Patent
Landgrebe et al.

(10) Patent No.: US 10,123,862 B2
(45) Date of Patent: *Nov. 13, 2018

(54) RANDOMLY UNIFORM THREE DIMENSIONAL TISSUE SCAFFOLD OF ABSORBABLE AND NON-ABSORBABLE MATERIALS

(71) Applicant: ETHICON, INC., Somerville, NJ (US)

(72) Inventors: Susanne Landgrebe, Suelfeld (DE); Daniel Smith, Dayton, NJ (US); Oliver Dick, Hamburg (DE); Leo Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 928 days.

This patent is subject to a terminal disclaimer.

(21) Appl. No.: 13/803,335

(22) Filed: Mar. 14, 2013

(65) Prior Publication Data

US 2014/0277576 A1    Sep. 18, 2014

(51) Int. Cl.
| | |
|---|---|
| *A61F 2/00* | (2006.01) |
| *A61L 27/16* | (2006.01) |
| *A61L 27/18* | (2006.01) |
| *A61L 27/48* | (2006.01) |
| *A61L 27/50* | (2006.01) |

(Continued)

(52) U.S. Cl.
CPC ............ *A61F 2/00* (2013.01); *A61L 27/16* (2013.01); *A61L 27/18* (2013.01); *A61L 27/48* (2013.01); *A61L 27/50* (2013.01); *A61L 27/56* (2013.01); *A61L 27/58* (2013.01); *D04B 1/16* (2013.01); *D10B 2509/08* (2013.01)

(58) Field of Classification Search
CPC . A61F 2/0063; A61F 2/00; D04B 1/16; A61L 27/16; A61L 27/18; A61L 27/50; A61L 27/56; A61L 27/58; A61L 27/48; D10B 2509/08

See application file for complete search history.

(56) References Cited

U.S. PATENT DOCUMENTS

| | | | |
|---|---|---|---|
| 4,105,034 A | 8/1978 | Shalaby et al. | |
| RE29,800 E | * 10/1978 | Gibson | ............ D02G 1/00 28/218 |

(Continued)

FOREIGN PATENT DOCUMENTS

| | | |
|---|---|---|
| DE | 3830005 | 11/1989 |
| DE | 3830481 | 6/1990 |

(Continued)

OTHER PUBLICATIONS

International Search Report re: PCT/US2014/019195 dated May 9, 2014.

(Continued)

*Primary Examiner* — Katherine M Shi
*Assistant Examiner* — Michael Mendoza
(74) *Attorney, Agent, or Firm* — Melissa J. Szanto

(57) ABSTRACT

An implantable structure, method for making the structure and method for using the structure, where the structure includes a combination of non-absorbable and absorbable components, and the implantable structure has a randomly uniform array of materials. The resulting implantable structure provides improved tissue ingrowth and flexibility after implantation and after absorption of the absorbable materials.

7 Claims, 6 Drawing Sheets

(51) Int. Cl.
*A61L 27/56* (2006.01)
*A61L 27/58* (2006.01)
*D04B 1/16* (2006.01)

(56) References Cited

U.S. PATENT DOCUMENTS

| | | | |
|---|---|---|---|
| 4,130,639 | A | 12/1978 | Shalaby et al. |
| 4,140,678 | A | 2/1979 | Shalaby et al. |
| 4,141,087 | A | 2/1979 | Shalaby et al. |
| 4,205,399 | A | 6/1980 | Shalaby et al. |
| 4,208,511 | A | 6/1980 | Shalaby et al. |
| 4,651,721 | A * | 3/1987 | Mikulich ............ A61F 2/26 600/40 |
| 4,942,875 | A * | 7/1990 | Hlavacek ............ A61F 2/06 606/230 |
| 5,464,929 | A | 11/1995 | Bezwada et al. |
| 5,595,751 | A | 1/1997 | Bezwada et al. |
| 5,597,579 | A | 1/1997 | Bezwada et al. |
| 5,607,687 | A | 3/1997 | Bezwada et al. |
| 5,618,552 | A | 4/1997 | Bezwada et al. |
| 5,620,698 | A | 4/1997 | Bezwada et al. |
| 5,645,850 | A | 7/1997 | Bezwada et al. |
| 5,648,088 | A | 7/1997 | Bezwada et al. |
| 5,698,213 | A | 12/1997 | Jamiolkowski et al. |
| 5,700,583 | A | 12/1997 | Jamiolkowski et al. |
| 5,711,960 | A | 1/1998 | Shikinami |
| 5,827,325 | A | 10/1998 | Landgrebe et al. |
| 5,859,150 | A | 1/1999 | Jamiolkowski et al. |
| 6,270,530 | B1 | 8/2001 | Eldridge et al. |
| 6,319,264 | B1 | 11/2001 | Tormala et al. |
| 7,112,210 | B2 | 9/2006 | Ulmsten et al. |
| 7,229,453 | B2 | 6/2007 | Anderson et al. |
| 7,285,086 | B2 * | 10/2007 | Smith ............ A61B 17/06066 600/30 |
| 7,901,415 | B2 | 3/2011 | Dauner et al. |
| 8,083,755 | B2 | 12/2011 | Mathisen et al. |
| 2005/0004427 | A1 | 1/2005 | Cervigni |
| 2005/0070930 | A1 | 3/2005 | Kammerer |
| 2005/0234291 | A1 | 10/2005 | Gingras |
| 2005/0244455 | A1 | 11/2005 | Greenawalt |
| 2005/0277942 | A1 | 12/2005 | Kullas et al. |
| 2005/0288797 | A1 | 12/2005 | Howland |
| 2006/0013863 | A1 | 1/2006 | Shalaby et al. |
| 2006/0058890 | A1 | 3/2006 | Lesh |
| 2006/0106419 | A1 | 5/2006 | Gingras |
| 2006/0233852 | A1 | 10/2006 | Milbocker |
| 2006/0264698 | A1 | 11/2006 | Kondonis |
| 2008/0119848 | A1 | 5/2008 | Shalaby et al. |
| 2009/0299408 | A1 | 12/2009 | Schuldt-Hempe et al. |
| 2010/0056857 | A1 * | 3/2010 | Nordmeyer ............ A61F 2/0045 600/30 |
| 2010/0152530 | A1 | 6/2010 | Timmer et al. |

FOREIGN PATENT DOCUMENTS

| | | |
|---|---|---|
| EP | 0325195 | 7/1989 |
| EP | 0252607 | 9/1992 |
| EP | 0628292 | 12/1994 |
| EP | 0923912 | 6/1999 |
| EP | 0774240 | 3/2003 |
| EP | 0878205 | 9/2006 |
| GB | 1097787 | 1/1968 |
| GB | 2222954 | 3/1990 |
| WO | WO 2005/074415 | 8/2005 |
| WO | WO 2006/092159 | 9/2006 |
| WO | WO 2010/077520 | 7/2010 |
| WO | WO 2011/082330 | 7/2011 |
| WO | WO 2011/103141 | 8/2011 |

OTHER PUBLICATIONS

Written Opinion re: PCT/US2014/019195 dated May 9, 2014.
International Search Report re: PCT/US2014/019197 dated May 2, 2014.
Written Opinion re: PCT/US2014/019197 dated May 2, 2014.
Feussner, H. et al. "Experimental Evaluation of the Safety and Biocompatibility of a New Antireflux Prosthesis", European Study Group Antireflux Surgery, Diseases of the Esophagus (2000), vol. 13, pp. 234-239.
Dietz, H.P. et al. "Mechanical Properties of Urogynecologic Implant Materials", Int. Urogynecol. J. (2003) 14, Published Aug. 5, 2003, pp. 239-243.
Lin, A. et al. "In Vivo Tension Sustained by Fascial Sling in Pubovaginal Sling Surgery for Female Stress Urinary Incontinence", The Journal of Urology, Mar. 2005, pp. 894-897, vol. 173.
Stein, H.J. et al. "Experimental Results with a Partially Absorbable Implant to Prevent Gastroesophageal Reflux", Recent Advances in Diseases of the Esophagus, Selected Papers in 6$^{th}$ Word Congress of the International Society for Diseases of the Esophagus, Aug. 23-26, 1995, pp. 733-738.

* cited by examiner

RANDOMLY UNIFORM THREE DIMENSIONAL TISSUE SCAFFOLD OF ABSORBABLE AND NON-ABSORBABLE MATERIALS

FIELD OF THE INVENTION

The present invention relates to an implantable scaffolding device for repair or augmentation of tissue, the device including a unique three-dimensional arrangement of absorbable and non-absorbable materials. The materials used, the structure of the device, and the method of making the device all provide improved benefits as an implantable device.

BACKGROUND OF THE INVENTION

Implantable scaffolds may be used to repair injured or traumatized body tissue, or to aid in the support of body tissue, such as, cartilage, skin, muscle, bone, tendon and ligament. These implantable scaffolds are intended to not only provide support to the repaired tissue, but also to promote and encourage tissue ingrowth so that the repair can be sustained in the body for an extended period of time. Typical scaffolds, however, include a high amount of non-absorbable materials, which remain in the body for a significant length of time, and may remain forever. Given the high level of non-absorbable materials, the scaffold may be felt by the user, or may complicate movement or flexibility.

Tissue scaffolds may be used for any number of applications, including, for example, repair applications such as tendon repair, pelvic floor repair, stress urinary incontinence repair, hernia repair; support applications such as bladder or breast implant support; tissue bulking; tissue augmentation; cosmetic treatments; therapeutic treatments; or generally as a tissue repair or sealing device. A scaffold may be made of solely non-absorbable materials, and will remain in its implanted location during and after tissue ingrowth. Such scaffolds will remain a part of the body in which it is implanted. Some scaffolds are made from entirely bioabsorbable materials, and over time will degrade and be absorbed into the body.

While some degree of non-absorbable materials may be desired, scaffold devices including non-absorbable materials may be felt by the user long after implantation, or may restrict movement or flexibility of the user after implantation. The present invention seeks to provide an implantable device that maintains desirable characteristics and less feel to an individual after implantation and absorption of certain components.

SUMMARY OF THE INVENTION

The present invention is directed to an implantable device for repair or augmentation of tissue, and method of making and using the device. The implantable device of the present invention is a unique three-dimensional arrangement of absorbable and non-absorbable materials to form a flexible three dimensional material having a soft or stiff feel, which can be made into a variety of thicknesses and densities. The design of the implantable device is initially uniform but appears random due to manufacturing processes, which provides a number of benefits and allows for greater and beneficial tissue ingrowth during absorption and once absorption is complete.

In one embodiment of the present invention, there is provided a method of forming an implantable device, including the steps of: forming a first yarn and a second yarn, where at least one of the first yarn and second yarns includes a first non-absorbable filament and at least one of the first yarn and second yarns includes a first absorbable filament, the first absorbable filament having a lower melting point than the first non-absorbable filament; forming an initial woven structure including the first yarn and second yarn; subjecting the initial woven structure to a first heat treatment at a first temperature sufficient to cause shrinkage of the first absorbable filament, and thus buckling at least the second yarn and forming an initial heated structure; heating the initial heated structure to a second temperature, the second temperature being higher than the first temperature, where at least a portion of the first absorbable filament is melted; and allowing the heated loose knit weave to cool to form a resulting implantable device.

In another embodiment, there is provided an implantable device having a random orientation of a non-absorbable filament, formed by the method including the steps of: forming a first yarn and a second yarn, where at least one of the first yarn and second yarns includes a first non-absorbable filament and at least one of the first yarn and second yarns includes a first absorbable filament, the first absorbable filament having a lower melting point than the first non-absorbable filament; forming an initial woven structure including the first yarn and second yarn; subjecting the initial woven structure to a first heat treatment at a first temperature sufficient to cause shrinkage of the first absorbable filament, and thus buckling at least the second yarn and forming an initial heated structure; heating the initial heated structure to a second temperature, the second temperature being higher than the first temperature, where at least a portion of the first absorbable filament is melted; and allowing the heated loose knit weave to cool to form a resulting implantable device.

In another embodiment, there is provided an implantable device including a contiguous weave of a buckled first non-absorbable filament and a first absorbable filament, where the absorbable filament has been subjected to shrinkage in threat least two dimensions, providing a random orientation of the non-absorbable filament.

Other embodiments provide an implantable material including a random orientation of at least one first non-absorbable filament held in place by a previously-melted first absorbable filament, in which the implantable material has a first elongation level prior to hydrolysis of the first absorbable filament and a second elongation level after hydrolysis of the first absorbable filament, where the second elongation level is at least five times as great as the first elongation level.

In still other embodiments of the invention, there is provided a method of reinforcing bodily tissue, including the steps of: forming a first yarn and a second yarn, where at least one of the first yarn and second yarns includes a first non-absorbable filament and at least one of the first yarn and second yarns includes a first absorbable filament, the first absorbable filament having a lower melting point than the first non-absorbable filament; forming an initial woven structure of the first yarn and second yarn; subjecting the initial woven structure to a first heat treatment at a first temperature sufficient to cause shrinkage of the first absorbable filament, thus buckling at least one of the first or second yarn, thus forming an initial heated structure; subjecting the initial heated structure to a second heat treatment at a second temperature, where the second heat treatment at least partially melts the first absorbable filament, thus forming a second heated structure; allowing the second heated structure to cool to form a resulting implantable device; securing the implantable device into the body of an individual; and allowing tissue ingrowth into the device.

The device may be single-layered or multi-layered, with one or more absorbable or non-absorbable components between layers.

BRIEF DESCRIPTION OF THE FIGURES

The Figures included herein are intended to be exemplary and not limiting as to the scope of the invention.

DETAILED DESCRIPTION OF THE INVENTION

Figure 1:
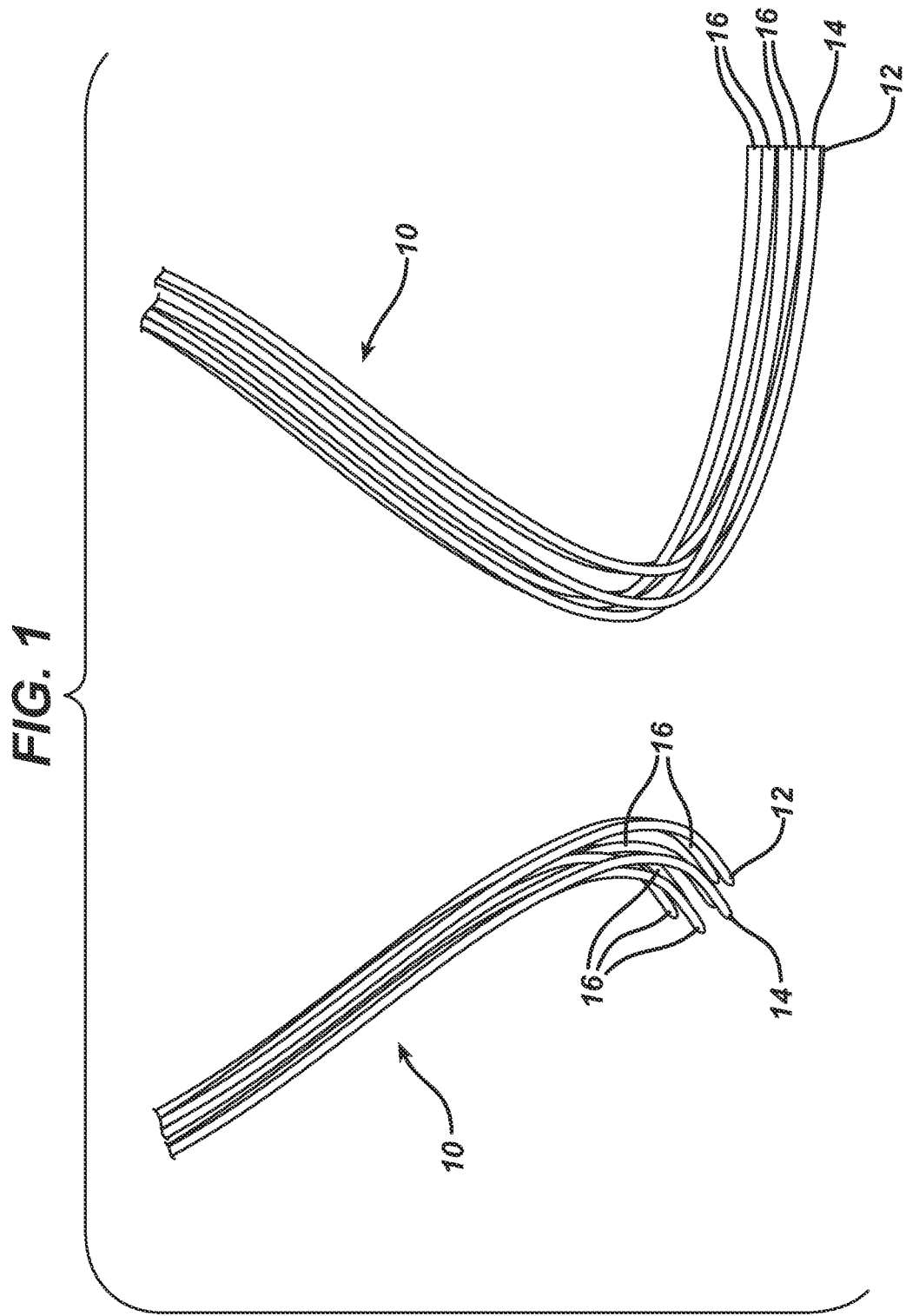
FIG. 1 is a depiction of a filament useful in the present invention, the filament being a multi-fiber filament.

In treatments to repair or support various tissue, it is often useful to include a scaffold, which may serve to not only support the tissue being repaired but also to provide a means to allow and promote tissue ingrowth and generation. The problem with most common mesh scaffolds is that they are generally made from substantially non-absorbable materials, and thus maintain their presence in the body long after implantation and after ingrowth of tissue. As used herein, the term "ingrowth" or "tissue ingrowth" refers to the generation and development of various bodily cells and tissues that grow in and around an implanted device over time. Any bodily tissues may be generated depending upon the site of the implant, including, for example, bone marrow, chondrocytes, osteoblasts, fibroblasts, angioblasts, smooth muscle cells, myocytes, endothelial cells, epithelial cells, hepatocytes and sertoli cells, among others. As used herein, the terms "bioabsorbable" and "absorbable" are used interchangeably, and refer to a material that is broken down and absorbed into the body, and which can be metabolized or excreted by the body over a period of time, such as from a period of minutes to at least a year.

The present invention provides a suitable implantable device, which has the suitable physical characteristics in all three dimensions, both prior to implantation and after tissue ingrowth has commenced. The present invention provides a scaffold that includes a low level of non-absorbable components, and yet maintains desirable characteristics after the bioabsorbable components have been absorbed and tissue has grown into the device. The resulting implantable material is initially woven, but does not have a set structure after the absorbable material is hydrolyzed. Further, given the unique structure and composition of the invention, the device is more tissue-like in its post-absorption state, allowing for natural tissue movement and less of a noticeable feel by the individual in which the device is implanted.

The present invention provides an implantable device, method of making the implantable device and method of using the implantable device. In preferred methods, the device is formed by initially selecting at least one, and more preferably, more than one polymeric fibers to form a filament, as will be explained in greater detail below. One example of a filament structure including a plurality of fibers is set forth in FIG. 1. One or more filaments may then be used to form yarns, which are generally described as kinked bundles of at least one filament. A filament can be made into a spool for easier use.

The one or more filaments may be kinked in any method, and in one method the filaments are used to form a tightly knitted structure, such as a sock or sheet. An example of a tightly knitted structure can be seen in FIGS. 2 and 2A. If a sock or sheet is first formed, the sock or sheet is subsequently unwound, which results in a kinked bundle of fibers containing the individual filaments that were used to weave the sock or sheet. Kinking can be achieved through other methods, such as via crimping devices. The kinked filament is termed a "yarn". In some embodiments, each spool of filament may be made into its own filament bundle, which can be made into a yarn. The initial filament may be a mono-fiber or multi-fiber filament, and the resulting yarn may likewise be mono-filament or multi-filament. Most desirably, yarns are formed through a plurality of filaments, each filament being kinked or crimped. Alternatively, yarns can be kinked or crimped after the filaments are formed into a yarn. Kinking or crimping of the filaments provides an increase in the volume of components in the device.

Figure 3:
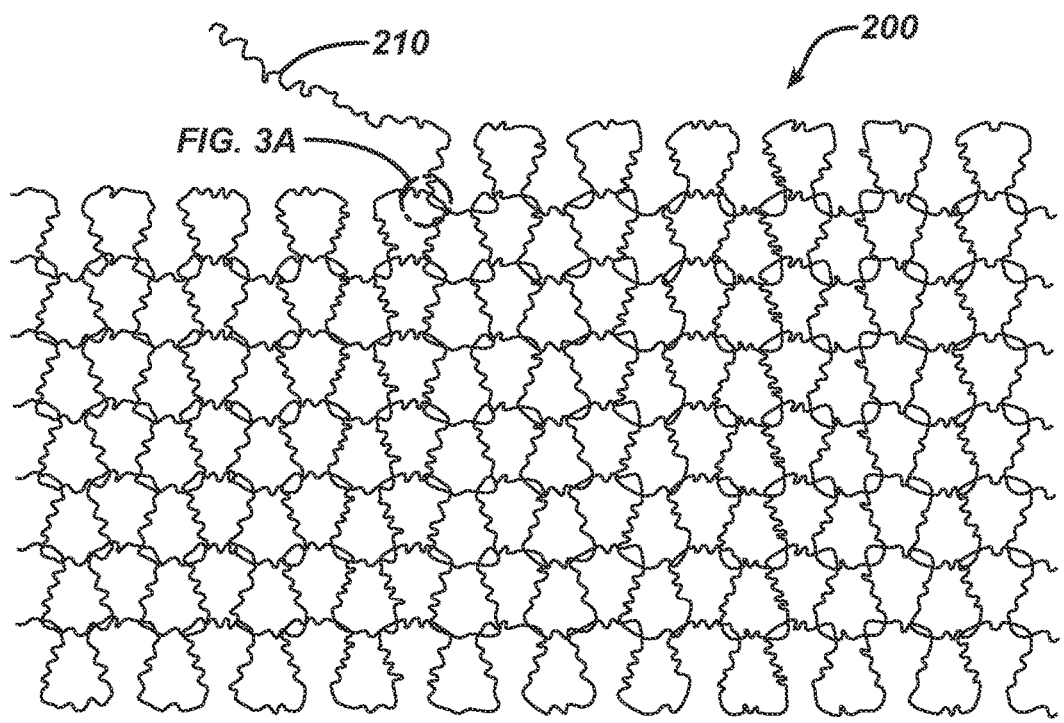
FIG. 3 is a depiction of an initial loose woven structure using yarns prepared from the knitted structure of FIG. 2.
Figure 3A:
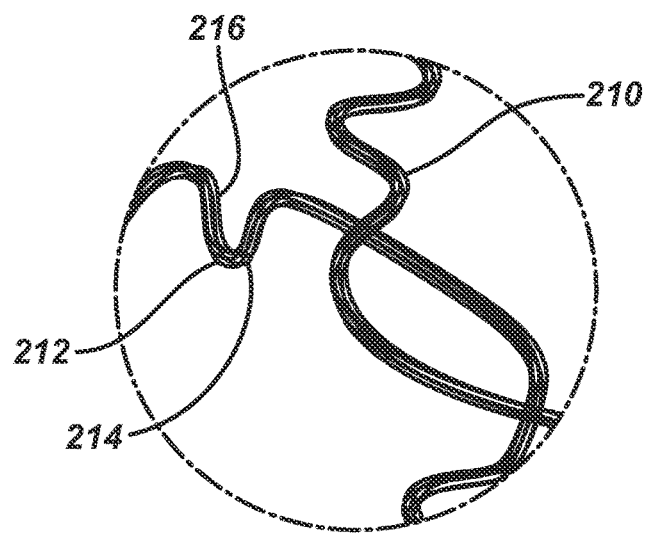
FIG. 3A is an expanded view of a section of FIG. 3.

The next step includes providing at least one yarn, and more desirably more than one yarn, and knitting those yarns together to form a loosely woven structure (referred to as an "initial woven structure"). One example of an initial woven structure is seen in FIGS. 3 and 3A. The initial woven structure is then subjected to one or more heating processes described below, shrinking at least some of the filaments in the structure and forming a resulting buckled and implantable structure, which may then be heat set. The resulting structure is also known as the "resulting implantable device", and refers to the final structure after being subjected to one or more heating steps. An example of a resulting implantable device can be seen in FIGS. 4 and 4A. Of course, there may be one or more intermediate structures between the initial woven structure and the resulting implantable device, for example, if multiple heating steps are used or during the heating process. After a first heating step, which shrinks at least some of the fibers in the initial woven structure, the resulting structure is termed an "initially heated structure". The initially heated structure may then be subjected to additional heating step(s) to melt some of the fibers and secure the shrunken and buckled structure in place. This forms the "resulting implantable device". After the resulting implantable device is implanted into the body of the user, it may be termed the "implanted device".

The present invention relates to an implantable device that includes a combination of non-absorbable fibers and absorbable fibers. As will be described in further detail below, the inventive device has a number of desirable physical characteristics, allowing it to serve as a viable and improved tissue repair or support device. For example, the device has a thickness in a desired range for the particular application for which it is being used. The thickness is such that the device is contiguous with ingrown tissue once ingrowth has taken place and the absorbable material has been absorbed by the body. The device further has a mass that is of a sufficient level to allow the predominant composition of new tissue to be generated body tissue. The device should also provide a suitable configuration so as to provide support while also allowing growth, i.e., the device has a suitable porous structure described below. In addition, at least the non-absorbable portion of the device should also be sufficiently interconnected, so as to avoid providing a device with fibers that may potentially migrate after implantation. The device may also have desirable physical strength, thus maintaining the integrity of the device after implantation, while not impeding ingrowth. In addition, the device should be sufficiently flexible, so as to allow the device to remain implanted and secured during normal bodily movement.

The inventive device is a three dimensional contiguous weave of non-absorbable and absorbable fibers, forming a distinctive orientation in all three dimensions. It is intended that the device have a randomly uniform non-structural array. As used herein, the term "randomly uniform non-structural array" is used to describe the orientation of the final product, which is formed by providing an initial uniform weave of at least two different fibers, one of which has a lower melting point than the other, which is subsequently drawn together in all three dimensions, thus generating the appearance of a randomized, non-oriented structure, even though the resulting structure had an underlying woven structure. The drawing together step will be described in detail below, and may include the step of raising the temperature to a level above the lowest melting point but below the highest melting point. The resulting structure may appear random and non-uniform, but in actuality it is uniform in its randomness. Put another way, the resulting structure may be a uniform flat three dimensional tight, heat set knit with undulating surfaces, which has the look and feel of a felt material. The resulting structure may be stiff, or may be somewhat flexible, depending upon the amount of material, layering, and density of resulting structure. The details of the resulting implantable device can better be understood by the description below. The use of a randomly uniform non-structural array is important in providing a device that enhances the growth and development of fibroblasts along and into the device over time. In addition, the resulting implantable device can be elongated with less effort than traditional non-absorbable scaffolds or meshes. Further, the invention, when absorbed into the body, creates a tissue-like repair, allowing for more free tissue movement than conventional scaffolds containing structural non-absorbable components.

In preferred embodiments, the device includes a weave of filaments including both non-absorbable and absorbable fibers, including at least one non-absorbable and at least one absorbable fiber. These filaments are formed into kinked yarns, which are woven together and subjected to the drawing steps described below. As used herein, filaments can be mono-fiber or can be multi-fiber filament materials, which may be, for example, braided or otherwise entwined. The term "filament" may include mono-fiber or multi-fiber filaments. As explained above, a "yarn" is formed from one or more filaments, which is kinked. The Figures set forth herein show multi-fiber filaments, but it will be understood that filaments may be mono-fiber.

The non-absorbable fibers of the present invention may be made of any stable, non-absorbable material. Suitable materials include, for example, polymers such as polypropylene (such as that sold under the tradename PROLENE suture, Ethicon, Inc., Somerville, N.J.), PVDF/HFP blends (such as a polymer blend of polyvinylidene fluoride and polyvinylidene fluoride-co-hexafluoropropylene sold under the tradename PRONOVA suture, by Ethicon, Inc., Somerville, N.J.), polyester, nylon, polyacrylate, polymethacrylate, cellulose acetates, non-biodegradable polyurethanes, polystyrenes, polyvinyl chloride, polyvinyl fluoride, polyvinyl imidazole, polyolefins, polytetrafluoroethylene (PTFE), silicon and styrene-block-butadienes, and combinations thereof. Other suitable non-absorbable materials include metals such as stainless steel, cobalt chrome, titanium and titanium alloys, and bioinert ceramics, such as alumina, zirconia, and calcium sulfate, and combinations thereof. The non-absorbable filaments of the present invention may include more than one non-absorbable fiber, which may be the same or may be different. Preferred non-absorbable fibers of the present invention include polypropylene, PVDF/HFP blends, polyesters and nylons. The non-absorbable fibers of the invention may be any size to serve the function of the implant, and particularly provide filaments that have a size between about 10 denier and about 100 denier, and more preferably from about 25 denier to about 60 denier. As used herein, the term "denier" has its understood meaning as a unit of measurement and is intended to be a unit of fineness for the filament (whether mono-fiber or multi-fiber filament), which is equal to the fineness of a filament weighing one gram for each 9000 meters of filament.

The absorbable fibers of the present invention may likewise be made of any desired bioabsorbable material. These bioabsorbable polymers include both synthetic polymers such as polyesters and biopolymers such as polypeptides, polysaccharides and derivatives thereof. Examples of suitable biocompatible, bioabsorbable polymers include but are not limited aliphatic polyesters, poly(amino acids), copoly(ether-esters), polyalkylenes oxalates, polyamides, polyacetals, polyketals, polycarbonates, polyorthocarbonates, polyurethanes, poly(alkylene succinates), poly(maleic acid), poly(methyl vinyl ether), poly(maleic anhydride)tyrosine derived polycarbonates, poly(iminocarbonates), polyorthoesters, polyoxaesters, polyamidoesters, polyoxaesters containing amine groups, poly(anhydrides), polyphosphazenes, biopolymers (e.g., collagen, gelatin, alginate, pectin, starch, fibrin, oxidized cellulose, chitin, chitosan, tropoelastin, hyaluronic acid and mixtures thereof) and mixtures thereof. Aliphatic polyesters may include, but are not limited to, homopolymers and copolymers of lactide (which includes lactic acid, D-L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, gamma,gamma-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Polyalkylene oxalates include those described in U.S. Pat. Nos. 4,208,511; 4,141,087; 4,130,639; 4,140,678; 4,105,034; and 4,205,399, each of which is incorporated by reference herein. The bioabsorbable materials useful in this invention further include polygluconate, poly(lactic acid-co-ethylene oxide) copolymer, polyphosphoester, polyamino acids, polylactic acid PLA), polyglycolic acid (PGA), polycaprolactone (PCL), polydioxanone (PDO), trimethylene carbonate (TMC), polyvinyl alcohol (PVA), copolymers, or blends thereof. Also useful may be polyphosphazenes, co-, ter- and higher order mixed monomer-based polymers made from L-lactide, D,L-lactide, lactic acid, glycolide, glycolic acid, para-dioxanone, trimethylene carbonate and epsilon-caprolactone. Polyanhydrides include those derived from diacids of the form $HOOC-C_6H_4-(CH_2)_m-O-C_6H_4-COOH$, where m is an integer in the range of from 2 to 8, and copolymers thereof with aliphatic alpha-omega diacids of up to 12 carbons. Useful polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150, which are each incorporated by reference herein. Other useful materials may include poly(L-lactide) ("PLA"), poly(d,l-lactide) ("PDLA"), poly(glycolide) ("PGA"), polycaprolactone, copolymers, terpolymer, higher poly-monomer polymers thereof, or combinations or mixtures thereof.

The fibers or filaments may be colored, such as through biologically stable dyes, or they may be uncolored. In some embodiments, at least one of the materials used in the resulting implantable device is provided with a color, such as through use of a dye, so as to allow a user to visually see the different fibers in the device. Further, the use of a colorant may provide a manufacturing and/or storage benefit, since the addition of a colorant in a material may render the material less sensitive to ultraviolet light. For example, one material in the device may be dyed with a blue or purple colorant.

Most desirably, the absorbable fiber or fibers includes one or more polymers selected from the group consisting of polymers made from glycolide and/or lactide, polyglactin 910 (sold under the tradename VICRYL suture by Ethicon, Inc., Somerville, N.J.), and polymers made from polyglycolic acid, poly(p-dioxanone) (such as that sold under the tradename PDS suture, Ethicon, Inc., Somerville, N.J.), caprolactone, trimethylene carbonate, and combinations thereof. Should synthetic absorbable polymers be used, desired polymers should be biocompatible and have degradation products that are low molecular weight compounds, such as lactic acid and glycolic acid, which enter into normal metabolic pathways. The bioabsorbable fibers in the present invention may be used to prepare filaments that have a size of from about 10 denier to about 100 denier and more particularly from about 28 denier to about 56 denier. There may be one or more than one bioabsorbable fibers in the present invention, and if multiple absorbable fibers are used, they may be prepared from the same material or may be prepared from different materials. Further, each fiber may have a different melting point than other fibers in the present invention.

In one embodiment, the present invention includes at least one non-absorbable fiber and at least one absorbable fiber, where the fibers have a different melting point than each other. In another embodiment, the present invention includes at least one non-absorbable fiber and at least two absorbable fibers, where each of the fibers has a different melting point than each other. Any of the absorbable fibers or non-absorbable fibers may have the lowest melting point in the device. In embodiments including at least one non-absorbable fiber and at least one absorbable fiber, the percent weight of the non-absorbable fibers to the total fiber weight is between about 5% to about 50% by weight, and more desirably from about 10% to about 25% by weight. Preferably, there is a higher level (by weight) of absorbable fibers than non-absorbable fibers in the device.

The device has a randomly uniform non-structural array, which describes the orientation of filaments in the device, particularly in all three dimensions. The device may be formed through any desired means, and in one embodiment, the device is formed through the following methods. Initially, fiber(s) are selected to form the device, and may include combinations of absorbable and non-absorbable fibers. These fibers are used to form individual filaments, which may include only one fiber (mono-fiber) or may include a plurality of fibers (multi-fiber). As can be seen in FIG. 1, a filament 10 includes a plurality of individual fibers 12, 14, 16. The filament of FIG. 1 shows a filament including three types of fibers: a first absorbable fiber (12), a first non-absorbable fiber (14) and a second absorbable fiber (16). As will be discussed in further detail below, there may be any number of different types of fibers in the filament in differing ratios. In this Figure, for example, filament 10 on the left side of FIG. 1 demonstrates a filament having one first absorbable fiber (12), one first non-absorbable fiber (14) and five second absorbable fibers (16), but any types and number of fibers may be used as desired. Filament 10 on the left side of FIG. 1 shows four second absorbable fibers 16, one first absorbable fiber 12 and one first non-absorbable fiber 14. Other varying amounts of material may be used, the amount may be measured by weight or by number of fiber strands.

Figure 2:
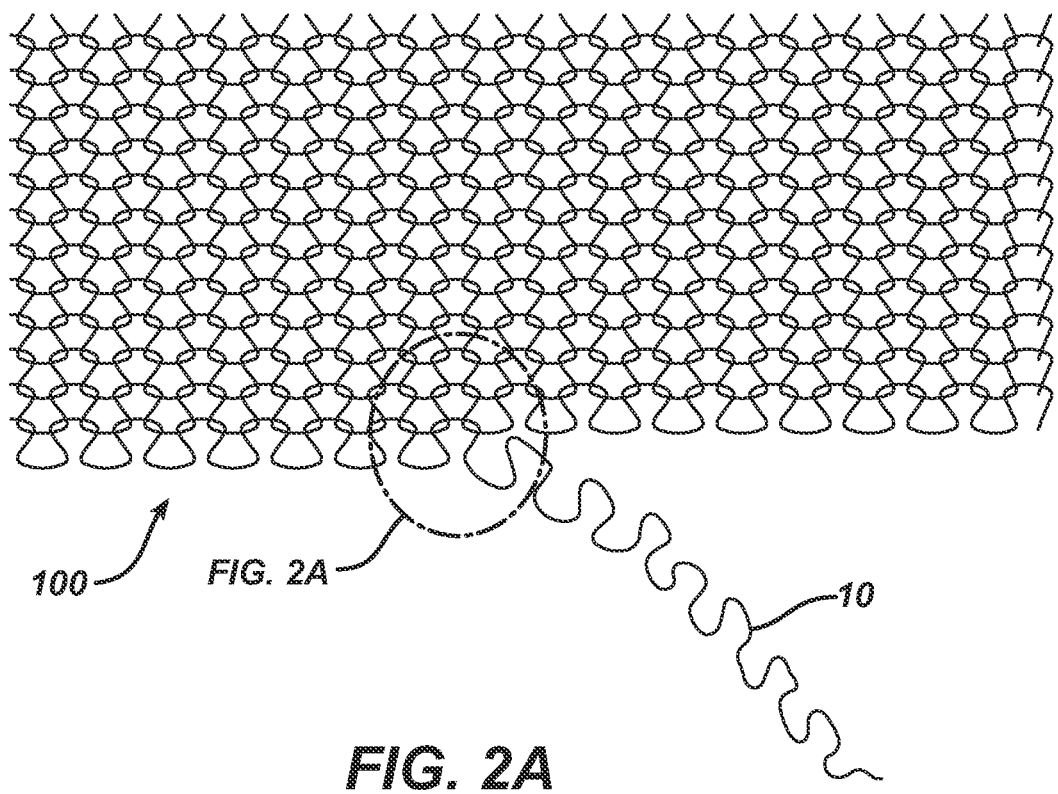
FIG. 2 is a depiction of an initial tightly knitted structure including a filament of FIG. 1.
Figure 2A:
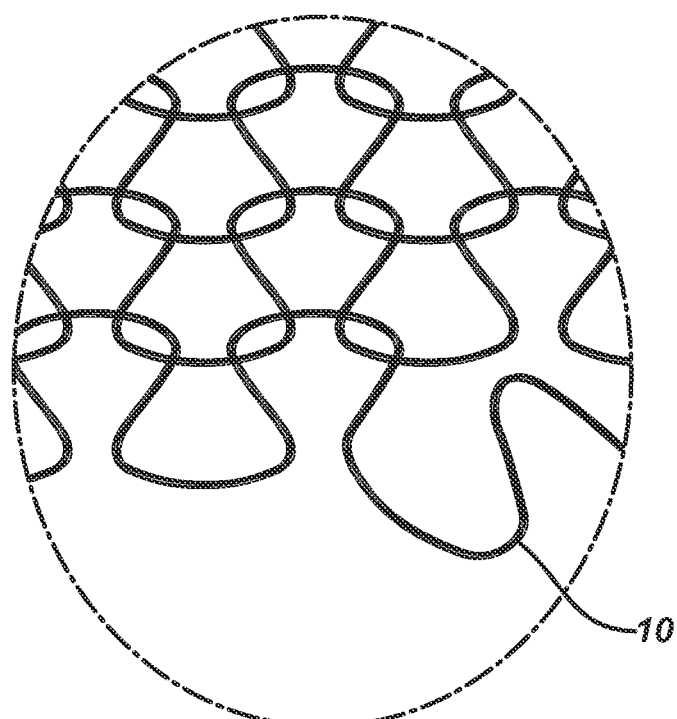
FIG. 2A is an expanded view of a section of FIG. 2.

Yarns are formed from various filaments, which may include the selected non-absorbable and absorbable fibers discussed above. Yarns may be formed through any desired yarn-forming means, and in some embodiments, yarns are formed through formation of an initial tightly knitted structure such as a sock or sheet. An embodiment of an initial tightly knitted structure can be seen in FIGS. 2 and 2A. FIG. 2 embodies a knitted structure 100 including one filament 10. The knitted structure 100 may include any number of different filaments 10 as desired. The filaments 10 selected may be tightly knitted so as to form the initial tightly knitted structure 100, which may be any size and shape desired. The resulting structure 100 may be formed into a continuous sock or sheet, which may have any desired length and diameter. For example, a sock may have a diameter of from about 0.5 inches to about 10 inches, and more desirably about 1.5 inches to about 5 inches. A sheet may be a substantially flat structure, having any length and width desired. The width can be, for example, from 0.5 inches to about 36 inches, and the length can be defined (e.g., at least about 12 inches) or can be extended to more than 5 feet, more than 10 feet, more than 20 feet, or even longer, allowing for a continuous sheet. If a sock or sheet is first formed, the sock or sheet may then be unwound so as to provide a kinked yarn of materials. Any number of yarns may be formed and used to form the implantable device. There should be sufficient yarn formed so as to weave the device to its desired size and shape.

In some embodiments, the initial fibers may be contained as a starting spool of fibers, which may be extruded from a homogeneous material and spooled. Of course, one fiber may be homogenous or may be made from multiple materials if desired. In some embodiments, there may be a bundle of very small fibers creating a small fiber bundle strand. The spool of fibers is used to prepare the filaments, which may then be used to prepare a yarn. If desired, one may take a plurality of spools of the same or different fibers, which may be formed into a filament or a bunch of fiber bundles. Yarns may be formed from any number of filaments (and thus any number of fibers), and it is possible that a yarn be formed from a single fiber. For example, yarns may be formed from filaments made from a plurality (e.g., about 3 to about 7) of fibers of a first absorbable material, such as polyglactin 910, an optional second absorbable fiber, such as PDS, and at least one non-absorbable fiber, such as polypropylene. Various combinations will be described below. The combination of fibers may be used to form an initial knitted sock or sheet, or the combination may be bundled and/or kinked and/or crimped through any desired means. If a sock or sheet is first formed, when the plurality of fibers are pulled together out of the knitted sock or sheet, the resulting yarn resembles a kinked bundle of fibers. Optionally, one may take one or more yarns from two different knitted socks or sheets to create the loose initial woven structure. As described herein, each yarn in the initial woven structure may contain various ratios of filaments having various ratios of absorbable and non-absorbable individual fibers, and it is preferred that at least one yarn contain a bundle strand of a non-absorbable fiber and at least one yarn contain a bundle strand of an absorbable fiber.

Once the yarn(s) are obtained, a woven structure is initially formed with the yarn(s) by loosely weaving yarns through any known method. A depiction of an initial loose woven structure can be seen in FIGS. 3 and 3A. This initial loose woven structure is referred to herein as the "initial woven structure". As embodied in FIG. 3, an initial woven structure 200 is made of a weave of at least one yarn 210, which may be made of a plurality of individual fibers 212, 214, 216. The initial woven structure 200 may be made of one type of yarn 210 or may be made of multiple yarns 210, each of which may be the same or may be different. FIG. 3 shows multi-fiber yarns 210, but it is understood that the yarns 210 may be mono-fiber yarns. As can be seen in FIG. 3, the yarns 210 have a kinked structure.

The initial woven structure 200 may be any shape desired, including, for example, rectangular, oval, or may even be tubular or conical in shape. The initial woven structure 200 may have any desired thickness, and is preferably between about 0.1 mm and about 5 mm thick, more desirably about 2 mm in thickness. Of course, the thickness may be modified depending upon the intended use and site of implantation. The initial woven structure 200 may have any length or width desired, and can be made into a large sheet of material. If the initial woven structure 200 is made into a large sheet, the resulting implantable device made therefrom may have a larger length and width that is desired, and the user may trim the device to the size and shape to be implanted. In some embodiments, the initial woven structure 200 itself can be implanted. The initial woven structure 200 will disperse the non-absorbable and absorbable fibers throughout the structure, desirably providing each measurable section of the structure with some absorbable and some non-absorbable materials present. The initial woven structure 200 has a substantially uniform appearance in all three dimensions. As used herein, a "loose weave" is intended to refer to a woven structure in which the ratio of courses to wales is from about 8 to 1 to about 1.5 to 1, and more preferably from about 5 to 1 to about 2 to 1. In some embodiments, however, the ratio of wales to courses may be from about 5 to 1 to about 1.5 to 1, and more preferably from about 5 to 1 to about 2 to 1.

The initial woven structure is then subjected to an increase in energy, such as through increased heat, radiation, vibration, electric current, radiofrequency, or other types of energy, intended to shrink the structure and to heat set the structure. In some embodiments, the initial woven structure 200 may be subjected to a first heating, which may be performed along with other energy variations, such as vibration or radiation exposure. The initial woven structure is first heated, such as by placement into a defined heating space, such as a heating apparatus or other space to provide heat to the initial woven structure 200. In some embodiments, the initial woven structure 200 is placed within a heating oven or in other embodiments it may be placed between first and second heating surfaces or plates. Desirably, the entire initial woven structure 200 is contained within the confines of the heating surface or surfaces, whether inserted into an oven or placed between heating surfaces, but if only a certain region of the initial woven structure 200 is to be heated, that region can be placed within the heating confines. Further, in some embodiments, the initial woven structure 200 may be formed into a tubular shape, such as by rolling in either the machine direction or non-machine direction, and placed within a tubular heating space.

If the initial woven structure 200 is placed in a heating source with defined surfaces, it is desired that the gap between those surfaces be at least slightly larger than the thickness of the initial woven structure 200, to ensure proper heating throughout the initial woven structure 200. Desirably, the gap between the surfaces is about 0.5 mm to about 5 mm, and more desirably about 1.5 mm and about 3.0 mm. Of course, the gap sizing between the heating elements may depend upon the thickness and density of the initial woven structure 200, or the type of materials used in the initial woven structure 200. If the initial woven structure 200 has about a 0.1 mm to about 1.0 mm thickness, for example, then the gap should be about 1.5 mm to about 3.0 mm. If the initial woven structure 200 has a smaller thickness, a smaller gap may be used, and vice versa. The gap size may be about 0.1 mm to about 2.0 mm greater than the thickness of the initial woven structure 200.

In this method of forming the implantable device, the initial loose woven structure 200 is subjected to at least one temperature, where the temperature is related to the melting point of the material having the lowest melting point in the structure. The material having the lowest melting point may be an absorbable material or may be a non-absorbable material. The below description refers to the material having the lowest melting point as being an absorbable material, but it should be understood that this material having the lowest melting point may be a non-absorbable material.

For this first heating of the initial woven structure 200, the temperature of the heating apparatus is set to a level that is: (1) at, (2) slightly above, or (3) slightly below the initial melting temperature of the material having the lowest melting point in the initial woven structure (this material is termed the "first fiber" in the device). This initial increase in temperature is the "first heating". As used herein, the term "slightly above" is from about 0.1° C. to about 10° C. greater than the initial melting temperature, or about 0.1° C. to about 5° C. greater than the initial melting temperature, and more desirably from about 0.1° C. to about 2° C. greater. Similarly, as used herein, the term "slightly below" is from about 0.1° C. to about 10° C. less than the initial melting temperature, or about 0.1° C. to about 5° C. less than the initial melting temperature, and more desirably from about 0.1° C. to about 2° C. less.

By way of example, the initial woven structure may include two fibers, the first fiber having an initial melting point of 100° C. and the second fiber having an initial melting point of 150° C. In this embodiment, the initial woven structure may be placed into a heating apparatus and exposed to a first temperature, the first temperature being about 100° C. (e.g., at the melting point of the fiber having the lowest melting point). Alternatively the first temperature may be from about 99.9° C. to about 95° C., more desirably from about 99.9° C. to about 98° C. (e.g., slightly below the melting point of the fiber having the lowest melting point). Or alternatively the first temperature may be from about 100.1° C. to about 105° C., and more desirably from about 100.1° C. to about 102° C. (e.g., slightly above the melting point of the fiber having the lowest melting point). This first temperature is intended to cause shrinkage. Melting of the fiber having the lowest melting point in the initial woven structure (e.g., the "first fiber", or if the fiber is an absorbable fiber, it may be termed the "first absorbable fiber") is not intended in this step, rather, shrinkage of the first material is intended.

In some embodiments, the first fiber is an absorbable fiber, which has an initial melting point of about 105° C., and the first heating stage is conducted at about 100° C. to about 103° C.

Further, it is desirable that the lowest melting point of the first fiber is at least 10° C. lower than the temperature of the material having the second lowest melting point in the initial woven structure. That is, the second fiber should have a melting point at least 10° C. higher than the first fiber.

For purposes of this disclosure, the first fiber (e.g., the fiber having the lowest melting point in the device) will be described as being absorbable, and may be referred to as the first absorbable fiber. The first heating is continued for a time period sufficient to cause shrinkage of the first absorbable fiber (having the lowest melting point in the device). Shrinkage of a material, as used herein, refers to restructuring of molecules in that material, but is not sufficient to melt the material. Shrinkage may be achieved, for example, by heating the material at its glass transition temperature. Melting of the first absorbable fiber is not intended, although slight melting may occur. Rather, the first heating stage is intended to cause initial shrinkage of the first absorbable fiber. Shrinkage, and not melting, is preferred because shrinkage allows the first absorbable fiber to retain some of its strength and pull on the other fibers in the device, whereas melting of a material reduces the pull strength of that material. Typically, this first heating stage should last about 10 to about 60 seconds, and more particularly from about 20 to about 45 seconds, but may vary depending upon the material or materials used in the initial woven structure. The shrinkage of the first absorbable fiber causes buckling of the resulting fibers in the initial woven device.

The resulting structure after the first heating stage is a device having a woven pattern of at least one yarn, which has fibers that have been buckled due to the shrinkage of fiber(s) having a lower melting point. Due to buckling, however, the structure appears to have a non-uniform array, since the degree of shrinkage is random. This resulting material is termed an "initially buckled structure" or an "initially heated structure".

The initially buckled structure may then be subjected to an optional further energy increase, or heating step ("second heating"), if desired, to heat set the device. A second heating step is preferred but is not required. This second heating may take place in the same heating apparatus described above or may be in a separate heating apparatus, and may include additional sources of increased energy, such as vibration or radiation, or other energy sources described above. The second heating is desirably at a temperature at or above the temperature of the first heating, and preferably above the melting point of the first fiber (having the lowest melting point in the device). The second heating may be at a temperature from about 2° C. to about 25° C. greater than the temperature of the first heating.

The second heating step is intended to melt the first fiber, which has the lowest melting point in the structure, thereby stabilizing the structure and dimensions of the initially buckled structure. This second heating step should be substantially rapid but may be slightly longer than the first heating, e.g., about 60 seconds to about 120 seconds, and more particularly from about 60 seconds to about 90 seconds. Longer second heating time may be required if, for example, a thicker device is desired. Optionally, the second heating step may include additional steps, such as a compression step, whereby the initially buckled structure is compressed between the heating elements during the heating stage. Compression may be desired, for example, if the shape of the initially buckled structure is to be altered so as to form the final resulting implantable device. It may be desirable, for example, to flatten the initially buckled device by about 25% to about 75% of its thickness, and more desirably by about 50% of its thickness (e.g., from about 2 mm in thickness to about 1 mm in thickness). The size of the gap between heating elements may be adjusted to the desired thickness, and pressure may additionally be exerted, if desired.

After being subjected to the first heating step and optional second heating step, the initially buckled structure is removed from the heating apparatus and allowed to cool, which may occur at room temperature or in a temperature-controlled environment (e.g., either above room temperature or below room temperature). In some embodiments, a heating device that has a cooling ability may be used, which allows for rapid cooling after heating is achieved. The resulting structure is a solidified, three dimensional, woven implantable device, where at least some of the filaments have been randomly buckled due to the shrinkage of some filaments. This is referred to as the "resulting implantable device". The resulting implantable device maintains its final shape due to the melting and subsequent solidification of some fibers, forming bonding points. The resulting implantable structure thus appears to have a random orientation in all three dimensions, although the non-melted filaments do, in fact, have an initial uniform weave. The resulting implantable device is in a woven/non-woven state, and appears and feels like a felt-type material. The resulting implantable device, therefore, has a "randomly uniform non-structural array" in all three dimensions of thickness, length and width. Further, given the random buckling of the melted filaments, the resulting implantable device appears to have a non-structural array of fibers.

Figure 4:
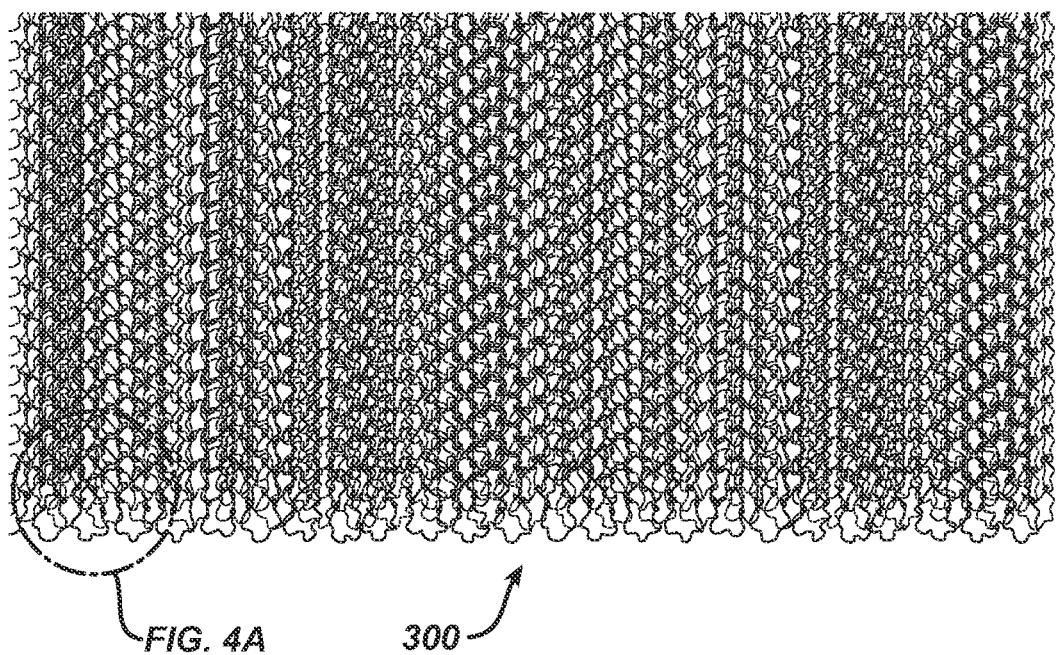
FIG. 4 is a depiction of an implantable device prepared from the initial loose woven structure of FIG. 3, after heating has occurred.
Figure 4A:
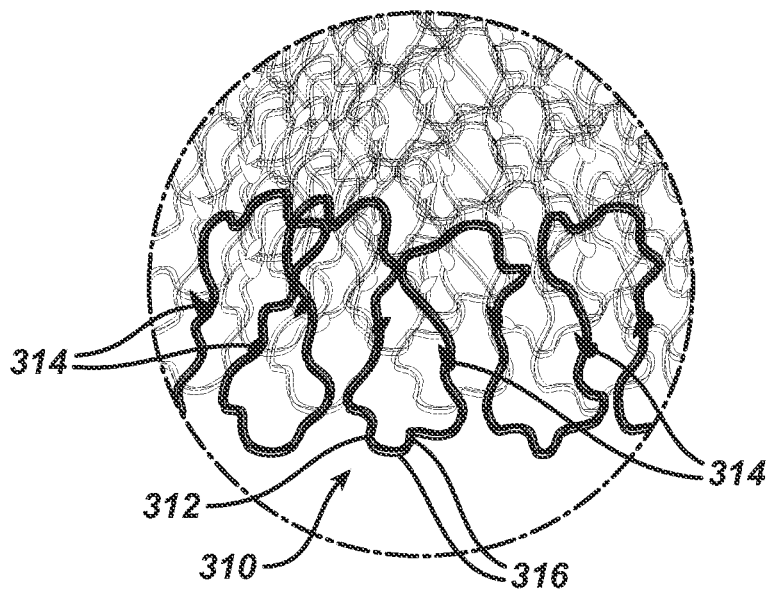
FIG. 4A is an expanded view of a section of FIG. 4.

An embodiment of a final, resulting implantable device is seen in FIGS. 4 and 4A, which show a resulting implantable device 300. The resulting implantable device 300 includes a shrunken weave of yarns 310, where each yarn 310 may be made of a plurality of fibers 312, 316. Kinked yarn 310 is essentially a kinked and shrunken version of the yarn 210 from FIG. 3. As explained above, there may be more than one type of yarn 310 used in the device 300, and each yarn 310 may be mono-fiber or multi-fiber. As can be seen in FIG. 4A, one of the fibers has been melted to form bonding points 314 in the device 300. The melting is achieved during the second heating step, where the fiber is melted and cooled to a sufficient degree to form secure bonding points 314 in the device 300. The resulting implantable device 300 is thus shrunken in at least two directions (e.g., length and width), and is held in place by the bonding points 314. The shrinking may result in a larger thickness, or, if shrinking is done in a compressed environment, the thickness may be reduced or remain substantially constant. Desirably, the bonding points 314 are formed from an absorbable fiber, e.g., the first absorbable fiber.

If desired, the final product to be implanted may include more than one layer of a resulting implantable device. More than one initial woven structure or initial buckled structure may be layered on top of one another and subjected to heating step (or steps) simultaneously, thus having multiple layers of resulting implantable material in a uniform cross pattern of random orientation that are fused together. Alternatively, each layer may be subjected to its own separate heating step(s), forming a plurality of resulting implantable devices, and then layered and secured to each other. The layers may simply be secured to each other directly, i.e., without any intervening components, or they may include material between them to enhance attachment. The attachment may be achieved through physical means, such as heat melting of components, or it may be achieved through chemical or physical means, such as via adhesive or sewing layers together. If desired, a film or films made from the material having the lowest melting point in the device (or alternatively, another low melting point absorbable material) may be placed between layers. A film used to layer the device may be absorbable. The layers may be placed into a heating apparatus, allowing the film to melt, thus increasing the bonding between layers. The layers may be identical to each other if desired; however, it is important to note that the various layers in the device need not be identical or even made from the same materials. Although each layer may include similar or overlapping materials, the exact compositions of each layer need not be the same. Alternatively, the materials in each layer may be wholly different, with no overlap of materials.

In some embodiments, there may be multiple layers of the inventive implantable device sandwiching a layer of mesh or a non-absorbable scaffolding material. In such embodiments, the layered material may be prepared by placing a layer of mesh or scaffolding material between a first layer of the initial woven device and a second layer of the initial woven device and then subjecting the sandwiched structure to heating steps as described above. Layers of adhesive material or of film may be placed between any layers to aid in preparing the layered structure. The sandwiched structure may then be subjected to heating steps as explained above, resulting in a layered heat set implantable device. In some embodiments, the layers may initially be made of a layer of mesh or scaffolding material disposed between a first layer of an initially buckled structure and a second layer of an initially buckled structure, and then the sandwiched structure may then be subjected to heating as described above. Any number of layers of material may be placed on top of each other, if desired, forming the layered device. The edges of the layers may be flush with each other, or at least one of the edges of a first layer may extend longer than the edge of a second layer, or vice versa.

The final device to be implanted may be made of multiple layers of the resulting implantable device, which may be laid in the same, different or alternate directions. Since the resulting implantable device has different elongation properties in perpendicular directions, layering the individual resulting device layers can create a device which has similar elongation properties in all directions. In some embodiments, depending upon the direction of the layers, the ultimate layered implantable device may be more capable of being elongated in a first direction and less capable of being elongated in a second direction. Multiple layering can create a very strong implantable device for various uses, for example, for tendon repair as opposed to soft tissue repair. Adding a film layer between resulting woven device layers, as described above, may serve to increase the bonding of layers, and can be pressed to a thickness smaller than the initial thickness.

In some embodiments, the material having the lowest melting point in the device (the first fiber) is an absorbable fiber, and may include poly(p-dioxanone) (including that sold under the trademark PDS suture by Ethicon, Inc., Somerville, N.J.). In such an embodiment, the first heating temperature may be about 100-103° C. and the second heating temperature may be from about 105° C. to about 120° C. Of course, the first and second heating temperatures may be varied depending upon the material or materials used in the device. In some embodiments, a higher second heating temperature may result in a greater level of flexibility and less tensile strength in the final resulting device. If used, poly(p-dioxanone) may be used in combination with another non-absorbable material and optionally other absorbable materials.

In one embodiment, the device may be made from three different fibers. The first fiber may be a non-absorbable fiber, such as polypropylene. The second fiber may be a first absorbable fiber, such as polydioxanone, and the third fiber may be a second absorbable fiber, such as polyglactin 910. Each fiber is made into a filament or may be bundled into a filament including multiple different fibers, and each fiber or filament may have its own denier. For example, the polyglactin fiber may have the smallest denier, and may be about 28. The polydioxanone fiber may have a slightly larger denier, such as about 30. The non-absorbable fiber may have the largest denier, such as about 60. The filament may be made of a number of fibers, and the resulting filament may have a desired denier. The level of kinking and buckling of the ultimate implantable device may be modified depending upon the material or materials forming the filaments. Other materials may be included as desired, or varying non-absorbable and/or absorbable materials may be used. Desirably, the device is made from at least one non-absorbable component (fiber) and at least one absorbable component (fiber).

In a multi-material embodiment, each material may be included in any desired amount or ratio. It is preferred, however, that absorbable fiber(s) be present in a greater amount than the non-absorbable fiber(s) in the device. For example, in one embodiment, the woven structure includes filaments of a first absorbable fiber and a first non-absorbable fiber, and the materials are present in amounts of about 1-7 parts (by weight) first absorbable fiber to about 1 part first non-absorbable fiber, and more desirably about 3-5 parts (by weight) first absorbable fiber to about 1 part first non-absorbable fiber. The ratios need not be by weight, and may be by individual fiber or yarn strand, regardless of the fiber denier. That is, there may be about 1-7 strands of first absorbable fiber to about 1 strand first non-absorbable fiber. In this embodiment, the first absorbable fiber may have a lower melting point than the first non-absorbable fiber, where the difference in melting point is at least about 10° C. Any materials may be used for this composition, including, for example, polyglactin 910 or poly(p-dioxanone) as the first absorbable fiber and polypropylene as the first non-absorbable fiber.

In another embodiment, the initial woven structure may include filaments of a first absorbable fiber and a second absorbable fiber, with the materials present in amounts of about 1-7 parts (by weight) first absorbable fiber to about 1 part second absorbable fiber, and more desirably about 3-5 parts (by weight) first absorbable fiber to about 1 part second absorbable fiber. Again, these ratios need not be by weight, and may be by individual fiber or yarn strand, regardless of the fiber denier. That is, there may be about 1-7 strands of first absorbable fiber to about 1 strand second absorbable fiber. In this embodiment, the first absorbable fiber may have a lower melting point than the second absorbable fiber, where the melting point of the first absorbable fiber is at least about 10° C. less than the melting point of the second absorbable fiber. Alternatively, the second absorbable fiber in the device may have a lower melting point than the first absorbable fiber. There may be a greater amount of this first absorbable fiber (e.g., the material having the lower melting point) than the second absorbable fiber, or vice versa. Any materials may be used for this embodiment, including, for example, poly(p-dioxanone) as the first absorbable fiber and polyglactin 910 as the second absorbable fiber.

In yet another embodiment, the structure may include three fibers, such as a first absorbable fiber, a second absorbable fiber and a first non-absorbable fiber or alternatively a first absorbable fiber, a first non-absorbable fiber and a second non-absorbable fiber. This embodiment may include a first absorbable fiber in an amount of about 1-7 parts (by weight), a first non-absorbable fiber in an amount of about 1 part (by weight), and a second absorbable fiber or second non-absorbable fiber in an amount of about 1 part (by weight). Again, these ratios need not be by weight, and may be by individual fiber or yarn strand, regardless of the fiber denier. That is, there may be about 1-7 strands of first absorbable fiber, about 1 strand first non-absorbable fiber, and about 1 strand of the second absorbable or non-absorbable fiber.

The three embodiments described above are exemplary and not intended to be limiting. The implantable device may include alternative or additional absorbable and/or non-absorbable fibers as desired. For example, there may be greater than three materials in the implantable device, including various combinations of absorbable and non-absorbable fibers. The starting materials may be used to form mono-fiber filaments or multi-fiber filaments, and the filaments in turn used to form yarns.

The individual yarns used to make the woven device may include any of the fibers described above and may be prepared in any desired means. In one embodiment, the yarns are formed by first making tight knits of the selected filaments, such as a sock or sheet, or through crimping the filaments. The initial tight knitted structure may include a filament including a first absorbable fiber and a first non-absorbable fiber, or alternatively a filament including a first absorbable fiber and a second absorbable fiber, or alternatively a filament including a first absorbable fiber, a second absorbable fiber, and a first non-absorbable fiber. The yarn or yarns may be formed from unwinding the tightly knitted structure, which results in a kinked bundle of filaments containing the individual fibers. Of course, more than one sock or sheet may be formed and more than one yarn can be formed from the sock(s) or sheet(s) prepared. Yarns may include absorbable fibers, non-absorbable fibers, and combinations thereof.

Once yarns are formed, the yarns may be used to form an initial woven structure. The initial woven structure may include weaves of any combinations of yarns, including those described above. In one embodiment, the initial woven structure may include a weave of only one type of yarn, for example, one yarn having a first absorbable fiber and a first non-absorbable fiber or a yarn having a first absorbable fiber, a second absorbable fiber, and a first non-absorbable fiber. In alternative embodiments, the initial woven structure may include weaves of at least two different types of yarns. For example, the initial woven structure may include a weave of a first yarn and a second yarn, where the first and second yarns are different from each other. The first yarn may be, for example, (a) a yarn having a first absorbable fiber and a first non-absorbable fiber, or (b) a yarn having a first absorbable fiber and a second absorbable fiber, or (c) a yarn having a first absorbable fiber, a second absorbable fiber, and a first non-absorbable fiber, and the second yarn may be, for example, (a) a yarn having a first absorbable fiber and a first non-absorbable fiber, or (b) a yarn having a first absorbable fiber and a second absorbable fiber, or (c) a yarn having a first absorbable fiber, a second absorbable fiber, and a first non-absorbable fiber, where the first and second yarns are made from different fibers. It is desired that the initial woven device include at least one absorbable fiber and at least one non-absorbable fiber.

By way of example, the initial woven structure may include a weave of a first yarn and second yarn, where the first yarn is made from a first absorbable fiber and a second absorbable fiber and the second yarn is made from a first absorbable fiber, a second absorbable fiber, and a first non-absorbable fiber. The particular absorbable and non-absorbable fibers in each yarn may be the same or they may be different. For example, in this embodiment, the first yarn may be made from polyglactin 910 and poly(p-dioxanone) and the second yarn may be made from polyglactin 910, poly(p-dioxanone) and polypropylene.

Another example is an initial woven structure including a weave of a first yarn and second yarn, where the first yarn is made from a first absorbable fiber and a second absorbable fiber and the second yarn is made from a first absorbable fiber and a first non-absorbable fiber. The particular absorbable and non-absorbable fibers in each yarn may be the same or they may be different. For example, in this embodiment, the first yarn may be made from polyglactin 910 and poly(p-dioxanone) and the second yarn may be made from polyglactin 910 and polypropylene.

These embodiments are intended to exemplify the various combinations possible, with the understanding that any of the absorbable and non-absorbable fibers identified above may be used. Alternative materials may be used if desired, including, for example, blends of various absorbable polymers, so as to give the resulting implantable structure a longer or shorter absorption profile. Absorption profile may be adjusted through post-manufacturing steps, such as sterilization, such as through exposure to gamma rays to reduce absorption profile. The presence of a non-absorbable component in the final implantable device may be useful, for example, to retain a presence in the body after absorption of the absorbable components. If complete absorption is intended and desired, however, a device including solely absorbable fibers may be used.

The initial shape or structure of the initial woven structure, before subjecting to any heating steps, may be a flat loose woven structure, as described above. Other shapes may be useful, including, for example, spherical, conical, cylindrical, and the like. It may be in the form of a bead or a connected set or string of beads, which may be connected via an absorbable or nonabsorbable filament material. Preferred embodiments are flat structures, the flat structures having a substantially rectangular or elliptical shape. Corners of the initial woven structure may be rounded, if desired. The resulting implantable device may be cut or trimmed by a user prior to implantation. As explained above, the final device to be implanted may include any number of layers of resulting implantable devices as desired, but the initial woven structures are typically formed as a single layer. If a multi-layered device is desired, the single layers may be combined with each other either prior to, during, or after various heating steps and using physical or chemical attachment means between layers. In addition, the layered device may include additional elements, such as a non-absorbable mesh or scaffold sandwiched between layers.

The resulting implantable device, after all heating steps, may have any length or width desired, depending upon the intended use. In some embodiments, the resulting implantable device may be in the form of a sheet, which may be trimmed to the desired size and shape by a user prior to implantation. In some embodiments, the device may be in the form of a strip of material, such as can be used for packing or modification of a previously placed SUI sling, or in other embodiments may be square shaped. The device may have any length and width desired, from 0.01 inches to greater than 12 inches. For example, if used as an SUI sling, the width may be from about 0.3 to about 0.7 inches and the length may be about 2 to about 4 inches as measured under the urethra. In other embodiments, the device may be circular or tubular in shape, and may have a diameter of from about 0.05 inches to about 10 inches. In elliptical configurations, the device may have a major radius of about 0.1 inches to about 5 inches and a minor radius of from about 0.01 inches to about 3 inches. In still other embodiments, the implantable device may have an undefined shape, such as an amorphous or cotton-ball type of configuration, which can be used as packing or filling material, such as to fill in a hole or void created through the removal of tissue in a patient.

The initial thickness of the initial woven structure may be from about 0.05 inches to about 0.5 inches thick, while the initial buckled structure, after the first heating step described above, may be from about 0.02 inches to about 0.25 inches thick, and the final implantable device, after all heating and optional compression steps described above, may be from about 0.01 inches thick to about 0.125 inches thick. In some embodiments, each heating step may reduce the thickness of the device, such as if compression is used.

The resulting implantable device has a distinct appearance when viewed by a user. The resulting implantable device is a closely constructed material mat, which either lacks or has only slight visual acuity, depending on the thickness and density of the construct. The external texture of the resulting implantable device is felt-like in nature. A felt-like material is comprised of short fibers matted together, whereas the inventive device has been initially loosely woven, and then an internal fiber connected to all the other fibers has been shrunk (via first heating) to contract and buckle the material into a compacted state of connected yet non-structural array of non-absorbable fibers. However, due to the post-shrinkage processing (e.g., a second heating step), the complete array of fibers in the resulting implantable device are locked together via at least one absorbable fiber which has melted and solidified. This gives the resulting implantable device a three-dimensional surface texture on a micro scale. The resulting implantable device has a woven/non-woven structure, which has a degree of porosity depending upon the material and the density of that material. It may be desired that the porosity of the resulting implantable device may not be capable of being seen by the user's naked eye, such as with typical loose weaves and meshes, while in other embodiments a user can see the porosity of the device with the naked eye. Pore sizes may be from about 4 microns in size to about 300 microns in size if compressed, but may be much larger (e.g., greater than 300 microns) if desired, for example, with no compression.

The resulting implantable device may have a desired stiffness. Stiffness may be measured by known tests, such as a bending test described in the Examples below. The force required to bend the inventive device may be from about 1 N to about 1.5 N, and more specifically from about 1.25 N to about 1.50 N. The resulting implantable device may have a tensile strength of about 5 N to about 4000 N, and more preferably between about 50 N and 500 N. The resulting implantable device may have a desired level of elongation when pulled in a first direction. The preferred elastic modulus of the resulting implantable device may be about 100 N/m to about 300 N/m, and more particularly between about 150 N/m to about 200 N/m.

Figure 5:
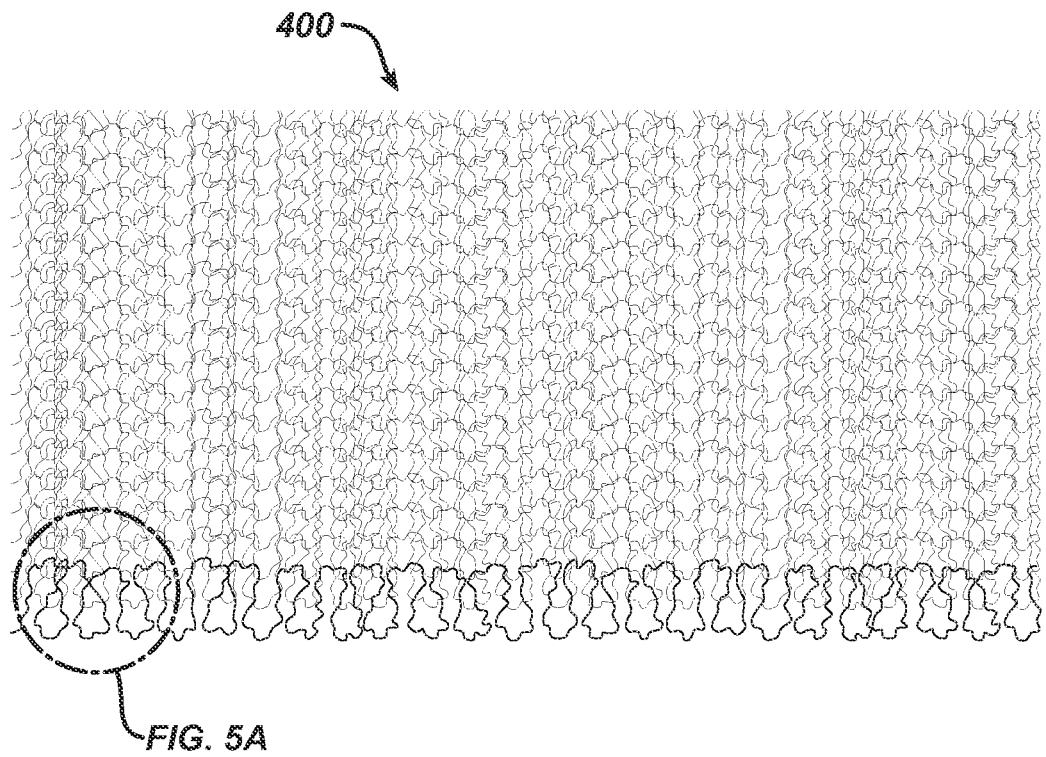
FIG. 5 is a depiction of the device of FIG. 4 after the absorbable components have hydrolyzed, and without tissue ingrowth.
Figure 5A:
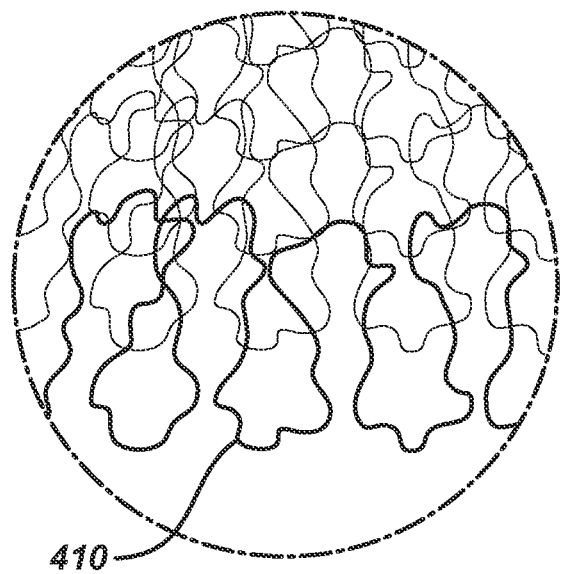
FIG. 5A is an expanded view of a section of FIG. 5.
Figure 6:
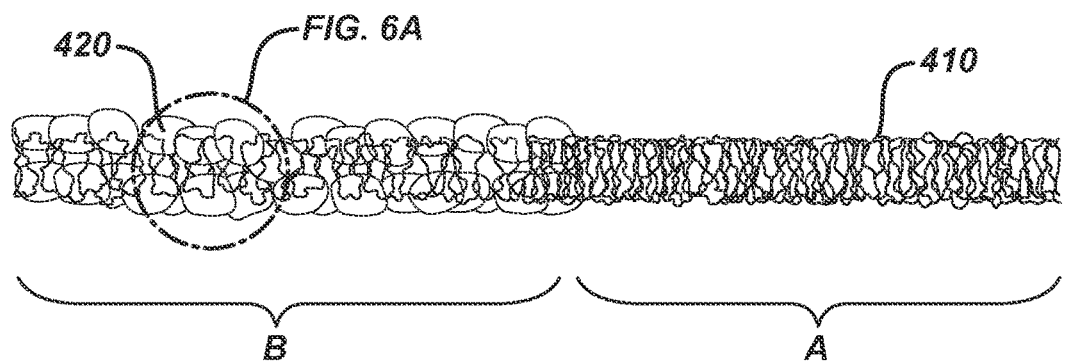
FIG. 6 is a side view of an implantable device after hydrolysis while maintaining its compressed shape, representing two hypothetical views of the device [A] without tissue ingrowth (i.e., bench hydrolysis) and [B] with tissue ingrowth (i.e., after implantation).
Figure 6A:
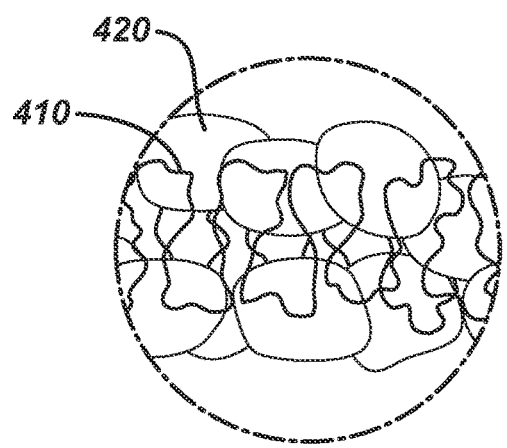
FIG. 6A is an expanded view of a section of section [B] of FIG. 6.

After the resulting implantable device is prepared, it can be implanted. Over time, hydrolysis of the absorbable fiber(s) in the device results in a final, hydrolyzed structure including only non-absorbable fibers. One embodiment of a hydrolyzed structure can be seen in FIGS. 5 and 5A, which depict a hydrolyzed structure 400 including only non-absorbable fibers 410. FIG. 6 is a cross-sectional view showing two hypothetical end results of a device: section [A] shows a hydrolyzed portion of a device including only non-absorbable fibers 410. This would be the result, for example, in an experimental or bench-top use, where there is no tissue ingrowth, and this section represents the polypropylene structure remaining in the same compressed state after hydrolysis. It is understood that the polypropylene structure may lose some compression after hydrolysis and may not have a compressed look. Section [B] of FIG. 6 shows a hydrolyzed portion after tissue ingrowth, where there is a combination of non-absorbable fibers 410 and tissue 420, which can best be seen in the expanded view of FIG. 6A.

It is understood, of course, that sections [A] and [B] of FIG. 6 are not both likely to be the end result after implantation, but rather these two sections are a side-by-side comparison of two potential results after [A] bench-top, or experimental hydrolysis and [B] tissue ingrowth. After implantation and absorption of the absorbable components into the body, it is intended that the entire device includes tissue ingrowth throughout it (e.g., section [B] of FIG. 6).

The present invention can provide multiple levels of elasticity for the device: a first level prior to any hydrolysis of components and a second level after hydrolysis of components. The implantable device (e.g., 300) has a first level of elasticity prior to hydrolysis of the absorbable material(s) in the device and formation of a hydrolyzed structure (e.g., 400). The first level of elasticity may be measured through any desired means, including a pull test in one or more directions. It is understood, of course, that the device may be more elastic in a first direction (e.g., along its length) than in a second direction (e.g., along its width). After hydrolysis of the absorbable material(s) in the device, such as after bench top hydrolysis, the absorbable material(s) in the device will be fully or substantially fully removed from the device, leaving only the non-absorbable material(s) (hydrolyzed structure 400). In this state, that is, after hydrolysis, the device has a second level of elasticity, which is greater than the level of elasticity of the implantable device prior to hydrolysis. In some embodiments, the level of elasticity of the device post-hydrolysis is at least twice the level of elasticity of the device prior to hydrolysis, and more desirably at least 3 times the level of elasticity of the device prior to hydrolysis, or at least 5 times the level of elasticity, or at least 10 times the level of elasticity. Any method for measuring elasticity may be used, but the method used should be the same for both pre-hydrolysis and post-hydrolysis. After implantation into the body of a patient, and subsequent absorption of the absorbable components of the device, there is tissue ingrowth into the device, which may restrict elasticity of the device post-implantation. The resulting device, with tissue ingrowth, is more elastic and flexible than a structured mesh or scaffolds made of structured meshes. This increased flexibility and elasticity is a significant benefit over structured mesh implants.

The present invention may be useful as an implantable device for the support or treatment of bodily tissue. The implantable device may be used as a tissue scaffold implant, which may be used for either reinforcing tissue structures or encouraging new tissue ingrowth to increase volumetric tissue presence in a particular bodily region. In some embodiments, the implantable device may be secured to a particular bodily tissue surface, including, for example, the pelvic floor, one or more tendons, bladder or breast, or it may be used to help treat ailments, such as stress urinary incontinence, hernia, and other similar ailments involving torn or compromised tissue. Implantation of the implantable device may be achieved through any standard and desired means, including, for example, by the use of adhesive attachment such as fibrin, or surgical attachment such as suturing or stapling. In some embodiments, the implantable device may be affixed into a location without any external means of attachment, such as when used as a packing material in a confined space or pocket where friction keeps the device in place. Securement should be sufficient to allow the implantable device to remain implanted in the intended site for a sufficient period of time to allow for tissue ingrowth to develop throughout the device, where the tissue ingrowth aids or provides the securement of the device. The attachment should be sufficient to keep the implantable device implanted at the site of implantation for at least one week, at least two weeks, at least one month, at least two months, at least six months, or at least one year.

After implantation, fibrin attachment and actual fibroblast ingrowth may begin within about seven to about fourteen days. Over time, the absorbable components will biodegrade and become absorbed by the body and the areas that contained these absorbable components will be filled with new tissue ingrowth. Since the resulting non-absorbable components have a non-discernible configuration and are present in such a low amount in the implantable device, as the absorbable components disappear the remaining materials in the device are not substantially felt by the user. This results in a resulting implanted device that provides support and provides a location for ingrowth, but also is comfortable to the user and provides a more natural tissue-like feel.

The mass of the implantable device may be any level that is sufficient to allow ingrowth of tissue into the device and thus result in the predominant composition being newly grown tissue. In some embodiments, the area weight before absorption of the absorbable materials in the implantable device may be from about 47 g/m2 to about 152 g/m2, and the resulting area weight after absorption of the absorbable materials in the device may be from about 12 g/m2 to about 40 g/m2. In embodiments in which there is a higher amount of absorbable material than non-absorbable material (e.g., about 10× as much absorbable material than non-absorbable material in the device, by weight), the ratio of the area weight prior to absorption to the area weight after absorption may be significantly increased. It is desired that the area weight after absorption be about 25% or less than 25% of the area weight prior to absorption. This is a marked improvement over other devices in which there is a higher amount of structured non-absorbable material in the implant.

The implantable device should also have a porosity suitable to allow for initial ingrowth of tissue after implantation, and the implantable device should be a "breathable material", allowing passage of gas through its body. Pores may extend through the entire thickness of the device, if desired. The porosity of the resulting implantable material may be altered depending upon the density of the starting material, and the "looseness" of the initial weave in the initial woven structure. In general, the looser the initial weave (e.g., the greater spaces between courses or wales), the lower the density of the resulting implantable device will be. It is intended that the areas where absorbable materials were contained will be at least partially filled with newly grown tissue during and after the absorption of the absorbable materials in the device.

The implantable device may include additional components, such as actives dispersed on or within the device, or the device may also be a carrier of drug, coagulant, or cell delivery/growth. Active components may be useful in treating the ailment or in delivering such active components for general healing. Radiopaque elements or markers may be included with the non-absorbable components of the implantable device, to aid in the implantation and positioning of the implantable device. The implantable device may additionally include one or more identifying markers, such as dyed sections or other indicia, to aid in implantation. The implantable device may include one or more additives that speed up or slow down the degradation and absorption of the absorbable material(s) in the implantable device, and may include encapsulating materials. Other useful and known components may be included in the implantable device, including, for example, nutrients, proteins, growth factors, bodily cells and tissues, immunomodulators, inhibitors of inflammation, regression factors, components to enhance or restrict tissue growth, and other drugs.

The present invention also relates to methods of repairing or augmenting tissue through use of the implantable device described above. The implantable device described above is prepared, and may then be implanted into the body by a user. The site of implantation is any desired site in the body, including, but not limited to sites for tendon repair, pelvic floor repair, stress urinary incontinence repair, or hernia repair. The site of implantation may be a site to provide support applications such as bladder or breast implant support. Alternatively, the site of implantation may be a site to provide any of tissue bulking, tissue augmentation, cosmetic treatments, therapeutic treatments, or generally as a tissue sealing or supporting device.

The method of repairing or augmenting bodily tissue can be achieved during a surgical operation to repair or augment the tissue. The site of implantation is first determined, and based upon the site and access to the site, the size and shape of the implantable device to be used may be determined. The implantable device could be sized and shaped to suit the particular geometry and dimensions of the portion of the tissue to be treated, and also should be sized and shaped to permit access through a surgical or other bodily opening. The implantable device may optionally be sized and shaped by a user prior to implantation, such as by cutting, folding, or otherwise manipulating the implantable device before implantation.

Once access is made into the desired anatomical site (whether by injury, surgical technique or any other means to provide access), the implantable device can be affixed to the desired location. The implantable device may be affixed through any desired means, such as through chemical fastening or mechanical fastening means. Chemical means may include adhesives such as fibrin glue or clot or other biologically-compatible adhesives. Mechanical fastening means include, for example, sutures, staples, tissue tacks, anchors, darts, screws, pins and arrows. Combinations of chemical and mechanical fastening means may be used if desired. In some instances, the implantable device may be fit into an opening such that friction is used to hold the implanted device in place. For example, in embodiments where the device has an amorphous shape and configuration, such as a filler material, the device may be fitted into an opening so as to fill the opening.

Once implanted securely and properly, the surgical site may be closed, if closure is required. If necessary, the implantable device may be removed and replaced into a different site, for example, if it is determined that the implantable device was improperly implanted. Once implanted into the site and allowed to begin absorption within the body, as a result of the normal healing process of the body, bodily tissue grows in and around the implantable device, eventually maturing into a tissue with similar mechanical properties as the native tissue. The mechanical nature of the implantable device also serves as a guide to tissue regeneration after implantation. In methods of augmenting tissue, for example, the presence of the implantable device guides new tissue to the locations of growth and development. New tissue grows around the periphery of the implantable device but also grows within the open pores of the implantable device so as to completely incorporate the implant.

Since the implantable device includes absorbable materials, and in particular, includes more absorbable material than non-absorbable material (by weight), after implantation, the absorbable material in the implantable device begins to degrade and become absorbed by the body into which it is implanted. Although the absorption process begins immediately after implantation, the absorbable material in the device begins to noticeably degrade and become absorbed by the body after a desired length of time, for example, after about one day, after about one week, after about two weeks, after about one month, after about two months, after about six months, or after about 1 year. The rate of degradation depends upon the materials used in the device and the amount/density of those materials in the resulting implantable device. Methods to increase the rate of degradation, such as radiation exposure, may be used after implantation to increase the rate of absorption. As used herein, the term "noticeably degrade" refers to the material being degraded and absorbed to a sufficient amount that the level of degradation would be detectable. The rate and level of degradation of the implantable device may be determined by bench top (laboratory) hydrolysis testing, or may be determined through invasive or non-invasive means after the device is implanted.

After the desired period of time and after noticeable degradation has occurred, the implanted device still includes some degree of mechanical structure and strength, but a portion of the absorbable material has been replaced with new tissue. Due to the unique three-dimensional orientation of absorbable and non-absorbable fibers disclosed above, after noticeable degradation and absorption, the implantable device results in a material having a continuous surface, thereby causing fibroblasts and other tissues to develop differently than they would into a typical mesh construct. In a typical open weave mesh product, fibroblasts grow along each mesh fiber and then across the mesh pores before growing through the mesh thickness. As the bodily tissues grow, they can reach over short distances and create a fibrous layer on each side of a mesh implant. This can be seen in animal studies where typical mesh implants are extracted during early time points such as 7, 14, or 21 days. In contrast, in the inventive device, the bond and tissue integration throughout the mesh pores and mesh thickness is greater as the time period increases, providing for improved tissue ingrowth and sustainability, and allowing for a more effective implant over time.

At the time of implantation, the implantable device has a contiguous weave of a yarn or yarns including at least one non-absorbable fiber and at least one absorbable fiber, where the initial contiguous weave extends in all three planes. In the resulting implantable device, the yarn(s) including a non-absorbable fiber has a first orientation, which is described as being a random uniform non-structural array. This first orientation is caused due to the buckling and shrinkage (and heat setting) of the melted absorbable material, thus creating the appearance of a random non-oriented structure. As the body begins to heal, new tissue begins to grow in and around the device. At the same time, the absorbable filament(s) of the implanted device begin to degrade and be absorbed into the body. After this degradation and absorption of absorbable fiber(s), the implanted device will develop open spaces due to the void created by the degradation and absorption. Concurrently, during the healing process, the spaces that were filled with absorbable material begin to become filled with new tissue.

During the beginning stages of tissue ingrowth and initial absorption of absorbable fibers, the implanted device substantially maintains the first orientation of non-absorbable fibers. The implanted device substantially maintains the first orientation of non-absorbable fibers for at least about one week, two weeks, one month, six months or a year. In some embodiments, due to tissue ingrowth, the implanted device will forever substantially maintain the structure and orientation of the non-absorbable fibers as was present in the resulting implantable device. In some embodiments, due to the ingrowth of tissue and the concurrent absorption of the absorbable fibers, the resulting orientation of the non-absorbable fibers may be random, and it may be compressed or expanded due to forces imparted by the new tissue.

As tissue ingrowth continues and the absorbable fibers continue to be absorbed and degraded, the new tissue may begin to move. This tissue movement is due to normal physiological conditions. Due to this movement and stretching, the initially hydrolyzed implanted device (which now has less absorbable fibers than when it was implanted due to hydrolysis and absorption) may begin to take on a second orientation. This second orientation is due to the movement of tissue, forcing the non-absorbable fibers to be moved. In this second orientation, the non-absorbable fibers provide little to no resistance to tissue movement, which is due to the random array of non-structural permanent material. As the absorbable fibers begin to be absorbed, the potential reshaping of the implanted device occurs due to tissue contractor and or tissue remolding. Tissue contractor happens during the healing period and may be due to implant security at implantation or surface fibroblast growth which has been seen in some test animal for both test and control articles. Tissue remolding happens at a longer term period (e.g., about 6 months). Tissue remolding is a weakening or a return of the newly formed scar tissue back to a state similar to before the injury or surgical intervention. If the implanted device included only absorbable fibers, tissue remolding might result in a need for a future tissue repair in the same area. However, due to the addition of non-absorbable materials in the inventive device, tissue remolding does not occur due to the presence of a foreign body (i.e, the remaining non-absorbable fibers). For this reason, the inventive device includes at least some non-absorbable fibers, but the level of non-absorbable fibers is minimal and non-structural so as to allow for the ingrowth and flexibility desired.

Over time, the implanted device may take on additional orientations due to continued growth, movement and stretching of new tissue, depending upon the strength of the tissue. If a non-absorbable mesh material is used in layered configuration with the inventive implantable material, there may be less flexibility after absorption of the absorbable materials. In instances where there is no additional mesh material and the implant includes only the inventive implantable device described herein, there will be greater flexibility and movement post-absorption, and the resulting site will be more tissue-like. Since natural body growth and movement inherently results in tissue movement and tissue growth, the random, non-aligned, non-structural buckled orientation of the non-absorbable fibers in the implant provides for an ultimately more flexible and more tissue-like environment than an implant constructed of a non-absorbable mesh or containing a mesh, even if that mesh component initially had flexural ability. In short, the inventive device provides for a significantly improved implant over time, allowing not only strength and improved ingrowth but also added flexibility and more comfortable feel.

After a desired length of time post-implantation (depending upon the particular absorbable fiber(s) used in the implantable device), which may be at least about one week, at least about two weeks, at least about one month, at least about two months, at least about six months, at least about 9 months, or at least about 1 year, the absorbable fibers in the implanted device are substantially degraded and absorbed by the body. After the desired length of time after implantation, such as at least three months, or at least six months, or at least one year, the implanted device is substantially free of absorbable fibers and consists essentially of non-absorbable fibers and new tissue grown therein. Although complete absorption of the absorbable fibers is desired, minimal amounts of absorbable fibers may remain (e.g., less than about 1% of its initial amount, less than about 2% of its initial amount, or less than about 5% of its initial amount), but the device consists essentially of non-absorbable materials and new tissue.

The device may remain in the body for any desired length of time, and may remain in the body through the life of the user. It is intended that the remaining portion of the device be integrated into the body of the user to a sufficient degree that it can remain within the body, making removal unnecessary. The newly grown tissue in and around the non-absorbable fibers of the device provides the desired support and strength to the site of implantation.

In summary, as explained above, in general, the implantable device is a woven device that includes non-woven characteristics, and is a non-mesh device, which is unique in that it is a felt-like material. The invention provides a structural device having a fairly uniform appearance upon implantation and prior to degradation of the absorbable components, however it is constructed in such a way that the initially loosely woven non-absorbable component is non-structural and expandable (ex vivo) once the absorbable fiber(s) of the device has been hydrolyzed. However, once absorption has completed and tissue has grown in and around the device, the non-absorbable component is tissue like.

This unique device may be created through the processes set forth above, and in one particular embodiment, the formation is a multi step process. First, the user selects the desired blend of absorbable and non-absorbable fibers from which to form the filaments in the device. Filaments may include only one fiber, or may include multiple bound fibers, where each fiber may be the same or may be different. The device should include at least one absorbable fiber and at least one non-absorbable fiber, although individual fibers forming the device may be solely absorbable or non-absorbable. For example, useful materials include fibers of polypropylene, PDS and polyglactin 910. The number or weight of specific fibers used in each yarn, and the number of yarns used to make the final resulting device may be modified as desired, and in preferred embodiments, the device includes at least one polypropylene fiber, at least one PDS fiber, and at least one to about 15 polyglactin 910 fibers. Various combinations of materials and ratios may be used as explained above.

Once the polymers to form the fibers are selected and the amounts of each fiber is selected, the individual filaments (whether mono-fiber or multi-fiber) are formed into a yarn, which is desirably a kinked filament, and which may be a kinked bundle of fibers. The yarn may be formed through any desired means, including simple crimping steps, or alternatively the filaments may be woven into a tight knit sock or sheet using a round knitting operation, and then the knitted sock or sheet can be unwound to provide the kinked filaments (yarns). Each yarn may include various combinations of components as explained above, for example, each yarn may include more than one type of filament, and each filament may include more than one type of fiber. Multiple socks or sheets or yarns may be used in the formation of the device, and each sock or sheet or yarn may include combinations of absorbable and non-absorbable components. It is desired that at least one yarn be used to form the device, and it is further desired that at least one absorbable fiber and at least one non-absorbable fiber be used.

From the yarns, a loosely knitted or woven initial structure is prepared. The initial loose structure can be any size or shape, as explained previously. The initial loose structure is then subjected to at least one heating step and more desirably two heating steps. The first heating step is at a temperature that is at or slightly below the melting point of the fiber having the lowest melting point in the device (the "first fiber" or "first absorbable fiber"). This first heating step shrinks the first fiber, causing buckling of the remaining fibers and forming an initially buckled structure (e.g., a heat shrinking step). Following this first heating, the initially buckled structure is subjected to a second heating step, which is at a temperature at or above the melting point of the first fiber in the structure. This second heating step is described in greater detail above, and is sufficient (both in temperature and duration) to melt the first fiber to a sufficient degree to cause the melted portions to bind the remaining fibers in the structure. The resulting material is cooled, whether in the same device used to heat the structure or after removal from the heating structure, forming the resulting implantable device. The resulting implantable device can be implanted as desired.

The size of the defined heated space, particularly during the first heating step, is relative to the type of absorbable fiber, amount or number of combined fibers and denier of fibers used in the loose weave. The size of the defined heating space can be another factor in determining the final density of the resulting material as well as the flexibility of the resulting material. In general, a larger defined space allows freer material movement, allowing the shrinkable fibers trapped in the weave to have a greater possibility of contraction (lowering frictional resistance), thus uniformly pulling greater quantities of absorbable and non-absorbable fibers into the defined heated space. In contrast, a smaller defined heated space will increase frictional resistance to movement, thus restricting contraction and resulting in less fibers being pulled in and lowering the resulting material density. The size of the defined heating space in the first heating step may thus be modified to provide for different levels of shrinkage and ultimate consistency of density and flexibility of the resulting implantable device.

The second heating step may be modified to increase or decrease the material strength properties, such as by applying compression during the second heating step. Not employing a compression may provide for a more fluffy, flexible, semi-structural material which may be suitable for packing or filling of space within the body where minimal strength or structure is needed. However, compression during the second heating step may be used to compress the material during the heat setting stage and give it a defined structure and orientation. This compression achieves at least two benefits: first, it melts at least one fiber or bundle to connect all the adjacent fibers through entrapment of the melting and pressure; and second, it can create any desired shape by compressing the material into a defined cavity under heat and pressure for a defined heating and/or cooling cycle. The resulting implantable device can have a range of tensile strengths and flexural strengths as well as defined shapes which, when stored in a controlled environment, such as in a sterile package or under nitrogen, will retain its material properties.

The resulting implantable device can be used immediately after formation, or it may be stored in a sterile environment. The device may be sterilized prior to packaging or prior to implantation. Further, the implantable device may be sized and shaped to a desired size and shape and packaged, or the implantable device may be packaged in a larger size so as to allow an end user to size and shape the device as needed. Sterile and substantially air- and fluid-tight packaging is important to avoid premature hydrolysis of the absorbable fiber(s) in the device. When the device is ready to be implanted, the user, typically a physician or assistant, opens the sterile and fluid-tight package, and sizes and/or implants the device as explained above. In embodiments where the device is a more fluffy, flexible, semi-structural material which may be suitable for packing or filling of space within the body where minimal strength or structure is needed, the user may remove only the amount required to fill a voided space within the patient's body.

As explained previously, the inventive device may be used for any number of uses and take any number of shapes, including, for example, in repair applications such as tendon repair, pelvic floor repair, stress urinary incontinence repair, hernia repair; support applications such as bladder or breast implant support; tissue bulking or general tissue filling; tissue augmentation; cosmetic treatments; therapeutic treatments; as a device to control uterine bleeding; or generally as a tissue repair or sealing device.

In one embodiment, the device can be used to control uterine bleeding. In this use, the invention may be used by creating adhesions within the uterus, which results in closure of the lower part of the uterus and ceases monthly bleeding. The method includes providing an instrument to prepare the area for implantation, such as increasing to a proper diameter and activating the endometrium. The method then includes providing an implanting an implantable device in the upper cervix/lower uterus area. The inventive device as explained above, including a combination of non-absorbable and absorbable components, may be used as the implant, and in particular the inventive device may be prepared into a cylindrical shape having a diameter related to the size of the cervix into which it is to be implanted. The cylinder may be formed by rolling a flat strip of inventive material and secondarily pressing to obtain the desired density to create the needed compressive forces to remain as placed and be effective, or by simply preparing a cylindrical shaped device. The device may include a suture or sutures extending the axial length of the cylinder, where the cylinder has at least one slit, and may include two slits, four slits, or more slits, and pulling on the filament or filaments compresses the cylinder (e.g., by pulling a first end towards a second end) after implantation to provide a more secure fit. A disk or plate may be secured so as to counter against upward movements. An applicator may be used to implant the device.

The resulting device may be used to create a urethral sling that delivers an immediate effect once placed, thus reducing the risk of bladder perforation and it having less foreign material left behind. In this embodiment, the implantable device may be placed in the connective tissue of the urogenital diaphragm or internus muscle for initial strong fixation of the implant. The cross section area can be either circular or rectangular or elliptic, and can change along the length of the implant. The implant part in the area below the urethra can be flattened. The tips at both ends can be stiffened by pressing or melting the fleece material under heat. A suture may be fixed inside the melted tip, inside of the fleece cylinders, or could be attached to the inserting instrument. Insertion sticks or applicator may also be used to effectively get the device to the site of implantation. The applicator can retain the device internally or externally through a variety of delivery means. This would also allow a pulling back of the implant. The ends of the implant can be made very stiff and can be punched or cut out in any necessary shape to increase the initial fixation in the tissue. The implant is intended to enter either the connective tissue of the urogenital diaphragm or the obturator complex which includes the obturator externous, internous and membrane. It may alternatively be located by or in contact with the pubic bone. Securement may be achieved by use of an affixation means, such as glues, adhesives, anchors, or compression into the connective tissue at that area. The application of adhesives can be delivered through a lumen within the device, applied, or expelled through an aperture or via the pores of the implant. The adhesive, if used, can be permanent or absorbable.

The device may be used as a barrier between a mesh implant and tissue, such as in an SUI implant or in any other device using a mesh implant. The device thus creates a new tissue layer serving as a barrier between the mesh and the vaginal wall. This may limit or avoid mesh erosion or exposure, reduce future pain and post operation corrective surgeries. Further, it may be useful to implant the inventive material between a mesh or the outer vaginal wall and the urethra to enable more pressure to be applied to the urethra. It may be a separate device positioned by hand, it may be pre attached to the mesh device prior to implantation, or may simply be applied with tweezers tucked under tissue prior to suturing the mesh in place.

The device may be used as an implantable pre-shaped external urethral device for mild SUI, such as for external bulking. This embodiment places the bulking externally to the urethral muscle and is compressive in nature at the mid urethra. The implant may be used such that it does not penetrate the urogenital diaphragm, but instead is placed below and/or around the mid urethra using only the surrounding tissue as initial support to maintain the kinking or external bulking effect. In some embodiments, the inventive material may be made into an implant, the implant having a first end, a second end, and a central section, where any of the first or second end or central section may be made of the inventive material. In this embodiment, the first and second ends may be sized and shaped so as to be suitable for implantation on either side if the urethra to provide support to the urethra. The immediate correction of SUI is created by compression of the urethra due to the external urethra bulking device, while the final tissue in-growth will create the permanent structure supporting the urethra. In this embodiment, both end zones of the device may be placed, or affixed, in contact to the lower edge of the pubic bone to create new permanent tissue straps for the long-term correction of SUI. The pre-shaped external urethra device for SUI can be formed into either V or U shape, and the first and/or second end may have a smooth or textured surface. The cross section area can be circular, rectangular or elliptic, and can change along the length of the implant. Additionally the center of the implant can be flattened if desired. The implant may be applied between the mid urethra and about one third of the distance from the bladder neck.

In some embodiments, a method of treating stress urinary incontinence may be provided, which may include the steps of making an incision in the anterior wall of the vaginal and placing the inventive material in a location between the outside of the urethra and the outside surface of the vaginal canal. In such embodiments, the material may be in a folded or elongated shape, or it may have an undefined amorphous shape, or it may be in a serpentine shape before or after insertion. The incision may be made at any desired location, and may be proximal to the mid-urethral location. A small degree of tissue plane dissection may be made at the location where the inventive material is to be placed.

The implantable device may be used for plastic surgery, for example, for filling defects such as cavities under the skin created by natural or surgical removal of tissue. This creates a permanent filling agent to correct the defect initially and with smooth natural visual properties with long-term effect. This embodiment additionally envisions use as a cosmetic fix to increase facial cheeks, remove aging lines or other cosmetic needs in strip, ball, string, plug, or particle form, where the particle form is created by chopping the inventive resulting material into small pieces such that the chopped material is extremely formable under the skin to eliminate seeing the implant outline. Due to the dry nature of particles and adhesive properties of the material, tissue ingrowth bonds the particles together, thus reducing spread of the filler beyond the location of placement, which often happens with liquid or gel type fillers.

The implantable device may be used for SUI treatment, where during the surgical sling treatment of SUI some patients are not cured to being completely dry, and therefore a secondary treatment such as bulking is necessary. The inventive device may be used for a secondary treatment instead of bulking to cause external compression on the urethra by packing the material into the area between the urethra and the previously placed sling. Due to the linear construction of the material it is less likely to migrate. Material can be packed into the tissue or be removed if needed for appropriate immediate result. The device may be in the form of strips, and kept on a reel. The device can be pressed into a desired opening by hand or with tweezers.

If the device is used for pelvic floor repair, for example, the vaginal canal may be opened and the inventive device inserted. For vaginal prolapse, the inventive material may be deployed between outer vaginal wall and surrounding structures. The device can be used as the inventive material or in conjunction with a mesh. A vaginal splint or other fixation device may be used to maintain the vagina in its anatomical position until sufficient ingrowth has occurred.

If used for breast repair or augmentation, for example, a light flexible bag-like sack may be made to allow insertion of the implant. This effect is to lessen or eliminate the movement of the breast implant during the healing and the normal tissue contraction phases of this surgery. Similarly such a sack may be used to repair and/or support soft organs such as the bladder. Further, due to its non-structural array of non absorbable contiguous fibers, the inventive device may be suitable for repair of tissue in children who have not yet fully developed.

In another embodiment, with the application of a film or barrier on one side of the implantable device such as PDS, the invention may be used with or without biologics for hemostatic control or as a tissue repair device that has tissue separation properties to avoid undesired adhesion of the repair site to surrounding tissue. The device may be formed into various shapes or configurations to serve as a tissue separator to avoid unwanted adhesions to surrounding tissue.

Other embodiments include using the implantable material into a straw-like form having a central lumen, which may be secondarily reformed to close off ends or create openings.

EXAMPLES

Example 1—Testing of Material after Implantation of 7, 14 and 28 Days

A study was conducted to test pullout force of the inventive material after implantation into rabbits. Samples of the inventive material (including fibers of polypropylene, polyglactin 910 and polydioxanone processed using a heating gap of 2.35 mm) and a control material (Gynemesh®), a non-absorbable polypropylene soft mesh implant) were implanted into rabbits. Two different sized implants were used for each of the inventive material and the control. The "small" implant was a 1.5 cm×1.0 cm sheet covered by a 1.0 cm×1.4 cm polyethylene sheath so that a 0.5 cm×1.0 cm section was uncovered. The "large" implants were sized to be 2.0 cm×1.0 cm, covered by a 1.0 cm×1.4 cm polyethylene sheath so that a 1.0 cm×1.0 cm section was uncovered. The sheath and implantable materials were ultrasonically welded. The sheath blocked or limited tissue ingrowth above the tissue plane and provided a place to grip the construct for testing after in vivo exposure. Two rabbits were assigned to each of the three time points and the six implants were made in each rabbit in the paravertebral musculature on either side of the spine. The control implant was placed in the left side and the inventive implant was placed in the right side.

After the desired time post-implantation, the pull-out testing was performed using lung grasping forceps and a 10 lb (50N) force gauge. The results are set forth in Table 1 below: I—large is the inventive sample, large size; C—large is the control sample, large size; I—small is the inventive sample, small size; and C—small is the control sample, small size.

TABLE 1

| | | Pull-Out Force (lbs) | | | |
|---|---|---|---|---|---|
| Time after implant | Data | I - large | C - large | I - small | C - small |
| 7 days | Average | 1.09 | 0.53 | 0.34 | 0.14 |
| | St. Dev. | 0.49 | 0.35 | 0.23 | 0.05 |
| 14 days | Average | 2.25 | 2.21 | 1.49 | 1.19 |
| | St. Dev. | 1.21 | 0.95 | 0.33 | 0.07 |
| 28 days | Average | 0.59 | 2.37 | 0.34 | 0.91 |
| | St. Dev. | 0.12 | 0.20 | 0.14 | 0.15 |

At 7 days post-implantation, the inventive material exhibited greater tissue ingrowth/fixation compared to the control for both sizes, as reflected in a greater than 2× force of resistance to pulling for the test articles. All tested articles were pulled intact from the tissue during testing. The initial differences in pull out force/tissue fixation may be explained by the surface contact area with tissue being greater for the inventive material than the control due to the textured contour of the former and open weave structure of the latter. In addition, there appears to have been equivalent structural stability at the time of implantation between the inventive material and control material (not shown in Table 1, but based on other tensile test results showing similarity in profile by design), yet there was 2 times greater tissue attachment providing resistance to movement between 'I' (large) and 'C'(large) at 7 days.

At 14 days post-implantation, the force values obtained within the Large and Small article groups were closer to each other than at 7 days. This apparent comparable resistance to pull could indicate an acceleration of tissue ingrowth for the control. However, the behavior of the different articles during testing suggests that the inventive material was actually better integrated at this time point. The inventive material either stretched during testing or separated completely at the tissue interface, leaving behind the ingrown portion of the test article in the tissue. All of the control articles were pulled completely from the tissue (after necking) at the same force value.

Beginning at 14 days post-implantation, the strength of the ingrowth was greater than the structural integrity of the absorbable test material as expected, hence the material separation during testing. The aspect of "pull force" is used for relative measurement of the degree of tissue ingrowth rather than a measure of pull resistance from a performance perspective as this material/device would never be 'pulled' from tissue in this manner.

At 28 days post-implantation, all structural components of the inventive material's fibers were degraded above the tissue plane and integrated into the tissue below the tissue plane. The large control articles tore at an average force comparable to the force to separate the large I articles at 14 days and not significantly substantially higher than the force to pull out the large control articles at 14 days. All inventive materials in both animals frayed or separated at the sheath/tissue interface resulting in lower pull out values than at 14 days. The testing behavior indicates that the unsheathed portion was well integrated into the tissue.

The inventive material (large) was believed to be a more representative test model than the small test. As can be seen in Table 1, the material I (large) achieved 48% (1.09 lbs) of its final 2.25 lbs at 7 days vs. 14 days, whereas the mesh control C (large) only achieved 24% (0.53 lbs) of its final 2.21 lbs at 7 days vs. 14 days. While the Inventive material I (large) achieved 98.2% (2.25 lbs) pull out force at 14 days verses the 2.37 lbs achieved by the control C (large) at 28 days.

As can be seen in the above table, the drop-in pull-out values after 28 days for the inventive material (I large) demonstrates a lower pull out force. This demonstrates the non-structural nature of the implantable device once the absorbable fibers are degraded after 28 days. There is less or equal pullout force to the 7 day control (using Gynamesh as the implant). This data demonstrates that once degradation occurs and the absorbable materials are replaced by tissue fiber, the implant is stable and if degradation was to occur without tissue integration, the implant would have no structural integrity, and the resulting hydrolyzed material would have a greater expansion profile than the initial, non-hydrolyzed implantable device. This further sets the inventive material apart from devices that use or integrate a mesh in which the mesh itself provides the structure to the implanted region.

Example 2—Testing of Area Weight, Non-Absorbable Material Amount, and Strength of Materials Preparation of Initial Woven Structures Three implantable materials were prepared, each with varying amounts of absorbable and non-absorbable materials. All knitting was conducted using Alveolar Tamponade processing parameters except for updated loop sizes for flat knitting determined pre-trial and shown below. For Alveolar Tamponade, two of the same round knitted tubes (socks) were produced first. Both tubes were then un-knitted in parallel and the resulting kinked filament yarn was flat knitted as an initial loose woven structure. The filaments used to make the materials included Vicryl®, which was dyed to show a purple color, PDS and polypropylene. Sock A was made with a first absorbable material and a second absorbable material. Sock B was made with a first absorbable material, a second absorbable material, and a first non-absorbable material. Sock C was made with a first absorbable material and a second non-absorbable material. Each tube was made using one of three ratios of materials, set forth below in Table 2:

TABLE 2

| Ratios of Materials in Knitted Socks | | |
|---|---|---|
| Sock A | Sock B | Sock C |
| 5 parts Vicryl ®, 28 denier | 5 parts Vicryl ®, 28 denier | 5 parts Vicryl ®, 28 denier |
| 1 part PDS, 30 denier | 1 part PDS, 30 denier | No PDS |
| No polypropylene | 1 part polypropylene, 60 denier | 1 part polypropylene, 60 denier |

The knitted socks were then unwound, providing kinked filaments of yarns. Yarns were prepared from these filaments. Yarns A, B and C each included the materials and ratios set forth in Table 2 above. Using these three yarns, three different initial loose weave structures (scarves) were prepared. The knitting parameters of Initial Woven Structures 1, 2, and 3 are set forth in Table 3 below. The raw material content of the three initial woven structures is set forth in Table 4 below. Finally, the raw material ratio is set forth in Table 5 below.

TABLE 3

Knitting Parameters of Initial Woven Structures 1, 2, and 3

| Structure No. | First Yarn | Second Yarn | Flat Knit Loop Size | Minimum Scarf Length |
|---|---|---|---|---|
| Initial Woven Structure 1 | Ratio A | Ratio B | 12.5 | 350 mm |
| Initial Woven Structure 2 | Ratio B | — | 12.5 | 400 mm |
| Initial Woven Structure 3 | Ratio A | Ratio C | 14 | 350 mm |

TABLE 4

Raw Material Content of Initial Woven Structures 1, 2, and 3

| Structure No. | # of Vicryl fibers (28 denier) | # of PDS fibers (30 denier) | # of polypropylene fibers (60 denier) |
|---|---|---|---|
| Initial Woven Structure 1 | 10 (280 denier) | 2 (60 denier) | 1 (60 denier) |
| Initial Woven Structure 2 | 5 (140 denier) | 1 (30 denier) | 1 (60 denier) |
| Initial Woven Structure 3 | 10 (280 denier) | 1 (30 denier) | 1 (60 denier) |

TABLE 5

Raw Material Ratio of Initial Woven Structures 1, 2, and 3

| Structure No. | Ratio of absorbable:non-absorbable | Total denier |
|---|---|---|
| Initial Woven Structure 1 | 5.7:1 | 400 |
| Initial Woven Structure 2 | 2.8:1 | 230 |
| Initial Woven Structure 3 | 5.2:1 | 370 |

As can be seen, Initial Woven Structure 1 includes a combination of two different yarns: Yarn A (a first and second absorbable material) and Yarn B (a first and second absorbable material and a first non-absorbable material). Initial Woven Structure 2 includes one yarn: Yarn B (a first and second absorbable material and a first non-absorbable material). Initial Woven Structure 3 includes a combination of two different yarns: Yarn A (a first and second absorbable material) and Yarn C (a first absorbable material and a first non-absorbable material). The number of fibers of each material is varied, and the resulting ratio of absorbable to non-absorbable material is set forth above. Initial Woven Structure 1 includes the highest amount of absorbable material compared to non-absorbable material and double the ratio of PDS used to shrink/kink the loose knit in the 1$^{st}$ heating step as compared to Initial Woven Structure #3, and Initial Woven Structure 2 includes the lowest amount of absorbable material compared to non-absorbable material.

Heating of Initial Woven Structures

Initial Woven Structures, as prepared above, were made into three 130 mm×130 mm sheets subjected to the 103° C. first heating step and the 105-120° C. second heating step, and each sheet was then cut into 6 strips for testing of density consistency across each sheet. Each strip was then evaluated as per the protocol including thickness measurements taken at 3 locations on each strip to evaluate shrinkage consistency at the various first heating distance gaps, where the first heating was conducted at approximately 103° C. for about 20 seconds. The shrinking was achieved by placing sheets of the Initial Woven Structures between two plates at a predetermined gap size between plates. Testing was conducted at different gap sizes: 2.35 mm, 1.85 mm and 1.35 mm. The resulting materials are termed "Initial Heated Structures". Subsequently, after the shrinkage, the Initial Heated Structures were then subjected to a second heating. The second heating was achieved using heated plates at a gap distance of 0.9 mm, for about 120 seconds, and at temperatures of either 105° C. or 120° C.

Weight of Resulting Heated Structures

Using the final resulting strips the average weight measurements were determined for each sheet and are reproduced in Tables 6A, 6B and 6C below.

TABLE 6A

Measured Weight of Strips from Resulting Structure 1

| Sheet No. | Gap: 2.35 mm | | Gap: 1.85 mm | | Gap: 1.35 mm | |
|---|---|---|---|---|---|---|
| | Weight (g) after second heating (105° C.) | Weight (g), after second heating (120° C.) | Weight (g), after second heating (105° C.) | Weight (g), after second heating (120° C.) | Weight (g), after second heating (105° C.) | Weight (g), after second heating (120° C.) |
| 1 | 0.642 | 0.683 | 0.525 | 0.533 | 0.452 | 0.462 |
| 2 | 0.692 | 0.653 | 0.537 | 0.547 | 0.470 | 0.453 |
| 3 | 0.642 | 0.627 | 0.540 | 0.542 | 0.462 | — |
| Weight (g/m$^2$) | 274.31 | 272.69 | 222.45 | 225.23 | 192.13 | 190.63 |

TABLE 6B

Measured Weight of Strips from Resulting Structure 2

| Sheet No. | Gap: 2.35 mm | | Gap: 1.85 mm | | Gap: 1.35 mm | |
| --- | --- | --- | --- | --- | --- | --- |
| | Weight (g) after second heating (105° C.) | Weight (g), after second heating (120° C.) | Weight (g), after second heating (105° C.) | Weight (g), after second heating (120° C.) | Weight (g), after second heating (105° C.) | Weight (g), after second heating (120° C.) |
| 1 | 0.382 | 0.375 | 0.325 | 0.323 | 0.268 | 0.265 |
| 2 | 0.363 | 0.375 | 0.318 | 0.317 | 0.250 | 0.255 |
| 3 | 0.355 | — | 0.320 | — | 0.257 | — |
| Weight (g/m$^2$) | 152.78 | 156.25 | 133.80 | 133.33 | 107.64 | 108.33 |

TABLE 6C

Measured Weight of Strips from Resulting Structure 3

| Sheet No. | Gap: 2.35 mm | | Gap: 1.85 mm | | Gap: 1.35 mm | |
| --- | --- | --- | --- | --- | --- | --- |
| | Weight (g) after second heating (105° C.) | Weight (g), after second heating (120° C.) | Weight (g), after second heating (105° C.) | Weight (g), after second heating (120° C.) | Weight (g), after second heating (105° C.) | Weight (g), after second heating (120° C.) |
| 1 | 0.433 | 0.487 | 0.400 | 0.387 | 0.342 | 0.343 |
| 2 | 0.445 | 0.455 | 0.380 | 0.378 | 0.347 | 0.348 |
| 3 | 0.427 | 0.447 | 0.393 | 0.395 | 0.345 | 0.345 |
| Weight (g/m$^2$) | 181.25 | 192.82 | 162.96 | 161.11 | 143.52 | 143.98 |

As can be seen, there was a statistical difference in the sheet weights when compared by material type and the gap size of the heating plates. The weight of the sheets was smallest in Resulting Structure 2, then increased in Resulting Structure 3, and finally was highest in Resulting Structure 1. This was expected due to the physical material content and ratio of components. In addition, the strip weight increased as the gap size increased, which reflects the allowance of more material to be fit within the gap space during shrinkage. That is, with a larger gap space, there is more space for material to accumulate. The impact of varying temperature did not show a common significant statistical difference across the Structures and gap sizes.

Thickness of Resulting Heated Structures

Using the sheets as heated above, the sheets were cut into 6 strips and each strip was measured at 3 locations; the average thickness measurements were determined and are reproduced in Tables 7A, 7B and 7C below.

TABLE 7A

Measured Thickness of Strips from Resulting Structure 1

| Sheet No. | Gap: 2.35 mm | | Gap: 1.85 mm | | Gap: 1.35 mm | |
| --- | --- | --- | --- | --- | --- | --- |
| | Thickness (mm) after second heating (105° C.) | Thickness (mm) after second heating (120° C.) | Thickness (mm) after second heating (105° C.) | Thickness (mm) after second heating (120° C.) | Thickness (mm) after second heating (105° C.) | Thickness (mm) after second heating (120° C.) |
| 1 | 750.4 | 709.2 | 732.9 | 700.1 | 703.2 | 673.1 |
| 2 | 779.1 | 669.3 | 742.6 | 692.5 | 699.8 | 671.5 |
| 3 | 747.5 | 714.6 | 728.4 | 694.3 | 712.2 | — |
| Weight (g/m$^2$) | 759.0 | 707.7 | 734.6 | 695.6 | 705.1 | 672.3 |

TABLE 7B

Measured Thickness of Strips from Resulting Structure 2

| | Gap: 2.35 mm | | Gap: 1.85 mm | | Gap: 1.35 mm | |
|---|---|---|---|---|---|---|
| Sheet No. | Thickness (mm) after second heating (105° C.) | Thickness (mm) after second heating (120° C.) | Thickness (mm) after second heating (105° C.) | Thickness (mm) after second heating (120° C.) | Thickness (mm) after second heating (105° C.) | Thickness (mm) after second heating (120° C.) |
| 1 | 638.7 | 628.5 | 597.5 | 593.7 | 552.1 | 538.2 |
| 2 | 653.1 | 608.7 | 591.2 | 584.1 | 533.7 | 534.2 |
| 3 | 640.6 | — | 574.4 | — | 553.3 | — |
| Weight (g/m²) | 644.2 | 618.6 | 587.7 | 588.9 | 546.4 | 536.2 |

TABLE 7C

Measured Thickness of Strips from Resulting Structure 3

| | Gap: 2.35 mm | | Gap: 1.85 mm | | Gap: 1.35 mm | |
|---|---|---|---|---|---|---|
| Sheet No. | Thickness (mm) after second heating (105° C.) | Thickness (mm) after second heating (120° C.) | Thickness (mm) after second heating (105° C.) | Thickness (mm) after second heating (120° C.) | Thickness (mm) after second heating (105° C.) | Thickness (mm) after second heating (120° C.) |
| 1 | 631.5 | 631.3 | 605.9 | 625.6 | 585.6 | 597.3 |
| 2 | 645.9 | 646.8 | 630.3 | 628.0 | 585.6 | 576.9 |
| 3 | 629.6 | 651.8 | 625.0 | 624.0 | 581.8 | 589.5 |
| Mean total (mm) | 635.7 | 643.3 | 620.4 | 625.9 | 584.3 | 587.9 |

As can be seen, there was a statistical difference in thickness when the material is changed and the gap size is changed. In general, the thickness of the material was smallest with Resulting Structure 2, and then increased with Resulting Structure 3, and Resulting Structure 1 provided the largest thickness. This may be due to the increasing physical material content (mass). The thickness also increased with the gap size increase, presumably because there is a larger space and allows for more material to be contained within that space. A statistical difference in thickness by temperature was only seen for Resulting Structure_1. Based upon the measurements taken, there is believed to occur a slight recoil after pressing, influenced by the mass of material being handled, the shrinkage gap, and the temperature of pressing. Temperature and pressure was equal for all samples.

Area Weight and Amount of Non-Absorbable Material in the Resulting Structures

For each of the three resulting heated structures formed as set forth above, the area weight of the structure was obtained and the amount of polypropylene (PP) content was obtained. Each measurement was taken for the different processing parameters, e.g., changing the gap size and changing the second heating from 105° C. to 120° C. The results are set forth in Table 8 below.

TABLE 8

Area Weight and Non-Absorbable Content in Resulting Structures

| | Gap size - 2.35 mm | | Gap size - 1.85 mm | | Gap size - 1.35 mm | |
|---|---|---|---|---|---|---|
| | Area Weight (g/m²) | Amount of PP (g/m²) | Area Weight (g/m²) | Amount of PP (g/m²) | Area Weight (g/m²) | Amount of PP (g/m²) |
| | Resulting Structure 1 (2 tubes, 10x Vicryl, 2x PDS, 1x Polypropylene) | | | | | |
| 105° C. | 274.31 | 41.15 | 222.45 | 33.37 | 192.13 | 28.82 |
| 120° C. | 272.69 | 40.90 | 225.23 | 33.78 | 190.63 | 28.59 |
| | Resulting Structure 2 (1 tube, 5x Vicryl, 1x PDS, 1x Polypropylene) | | | | | |
| 105° C. | 152.77 | 39.85 | 133.80 | 34.90 | 107.64 | 28.08 |
| 120° C. | 156.25 | 40.76 | 133.33 | 34.78 | 108.33 | 28.26 |
| | Resulting Structure 3 (2 tubes, 10x Vicryl, 1x PDS, 1x Polypropylene) | | | | | |
| 105° C. | 181.25 | 29.39 | 162.96 | 26.43 | 143.52 | 23.27 |
| 120° C. | 192.82 | 31.27 | 161.11 | 26.13 | 143.98 | 23.35 |

The amount of Vicryl and PDS was also determined for each of the structures set forth above, and the material ratios were determined. For Resulting Structure 1, there was found to be about 70% Vicryl, about 15% PDS and about 15% polypropylene. For Resulting Structure 2, there was found to be about 60.9% Vicryl, about 13% PDS and about 26.1% polypropylene. For Resulting Structure 3, there was found to be about 75.7% Vicryl, about 8.1% PDS and about 16.2% polypropylene.

As can be seen, the area weights are lowest in Resulting Structure 2, followed by an increase in Resulting Structure 3, and the largest area weight can be seen in Resulting Structure 1. For all Resulting Structures, the amount of polypropylene increased with increasing gap size. The Structure with the lowest polypropylene amounts were Resulting Structure 3. This is likely due to that structure having a lot of Vicryl versus one strand of PDS contained in Resulting Structure 1. Since all strands are together less PP gets pulled into the first heating gap. Similarly Resulting Structure 2 and Resulting Structure 1 have equal ratios of material (Vicryl and PDS) so the percentage of PP was also equal in general.

Tensile Strength of Resulting Structures

The three Resulting Structures were prepared as explained above, each prepared at gap sizes of 2.35 mm, 1.85 mm, or 1.35 mm and at second heating temperatures of either 105° C. or 120° C. Each resulting strip was measured with a ZWICK tester to assess any difference in the tensile strength. The level of stress (N) was measured at 1% strain and at 10% strain.

It was found that there was a statistical difference in tensile strength for all three material types when the temperature was changed, regardless of gap size. In general, the lower temperature of second heating was seen to produce a greater tensile strength and a smaller confidence level (standard deviation) for each gap size. The additional melting of the PDS at the higher temperature may influence the outcome. There was a statistical difference in tensile strength due to gap size only for the Resulting Structures formed at a 120° C. second heating. In general, when the second heating was 120° C., as the gap size increased, the tensile strength increased. The Resulting Structures formed using the lower second heating (105° C.) did not show a significant change in tensile strength due to gap size change. Resulting Structure 1 was found to have a statistically higher tensile strength than both Resulting Structures 2 and 3 formed at the same heating temperature and using the same gap size. The amount of PDS content and level of melting of the PDS may provide a driver of tensile strength of the resulting material. Additional PDS may provide an increase in the shrinking effect during the heating stages, thus providing an increase in tensile strength. In effect, the PDS acts as a "glue" for bonding the materials together. However, the decline in tensile strength as the temperature increased demonstrates that increased melting of PDS may have a detrimental effect.

In sum, it appears that Resulting Structure 1 provided a significantly different final product than Resulting Structures 2 and 3. It can also be seen that, in addition to the types and ratios of materials present, the gap size during heating may provide a statistical effect in the weight, strength and thickness of the final resulting product. The increase in temperature had some effect, most noticeably on tensile strength.

Example 3—Porosity and Stiffness Testing

Inventive structures were prepared and tested for porosity and for bending strength, or stiffness. The inventive structure used for this example included vicryl, polypropylene and PDS in a ratio of 5 parts (by weight) vicryl, 1 part polypropylene (by weight) and 1 part PDS (by weight). The initial loose woven structure was prepared, and was subjected to a first heating at 103° C. in a 1.5 mm gap. The initial heated structure was then subjected to a second heating at 105° C. in a 0.9 mm gap, providing the final resulting device. The resulting device was substantially flat and had a board-like shape.

Stiffness of the device was measured using a three-point bending stiffness test, specifically using a Zwick Roell tensile test. For this testing, a trapeze shaped indenter was pressed onto a test section of the inventive device, measuring about 50 mm×50 mm, where the device was placed over a 12.5 mm gap. The gap allowed the test section to be pressed down by the indenter as far as necessary to examine the maximum force the sample can endure before it begins to enter the gap. Four samples of the inventive device were tested. As a comparison, two known products (Ultrapro Mod®, a polypropylene/poliglecaprone 25 device, and Prolene Softmesh®, a polypropylene mesh) were tested using the same parameters. The four samples were each tested in both directions plus three repetitive measurements in order to test for reproducibility. Stiffness testing resulted in a maximum force of 1.351 N for the inventive device, with a standard deviation of 0.2789. This is significantly higher than the stiffness tested for other known products (Ultrapro, 0.38 N; Prolene Softmesh, 0.25 N).

Porosity, which refers to the pore size distribution, was measured using a POROLUX 1000 device. To measure the porosity, a circular section of inventive device having a diameter of about 18 mm was soaked in Silpore, a high density liquid. Gas was then pushed through the sample, while a machine recorded the gas flow and pressure. Due to surface tension, the largest pores open first, followed by the next smallest pore and down to the smallest pore. Results are calculated into a gas flow over pore size graph.

Five samples of the inventive device were tested, and measured for largest pore size and smallest pore size. The largest pore size for sample 1 was 218.1 microns, and the smallest pore size for sample 1 was 10.49 microns. The largest pore size for sample 2 was 254.2 microns, and the smallest pore size for sample 2 was 10.78 microns. The largest pore size for sample 3 was 246.0 microns, and the smallest pore size for sample 3 was 5.24 microns. The largest pore size for sample 4 was 21.38 microns, and the smallest pore size for sample 4 was 4.18 microns. The largest pore size for sample 5 was 236.1 microns, and the smallest pore size for sample 5 was 4.29 microns.

As can be seen, on average, the largest pore size was 233 microns in diameter, and the smallest pore size was about 6 microns in diameter. The distribution of pores sizes was fairly homogenous through the five samples tested.

Example 4—Elongation Testing Post-Hydrolysis

Various structures, including the inventive structure, were tested for elongation properties. To achieve the elongation, various samples of the inventive structure (both in the implantable state and after hydrolysis has occurred), hydrolyzed VYPRO® (about 1.5 cm long×2 cm wide), hydrolyzed Ultrapro® (about 5 cm long×1 cm wide), and a non-absorbable polypropylene mesh product (Gynemesh®) (about 5 cm long×2 cm wide) were provided. Measurements were taken for one sample of implantable device prior to implantation (about 5 cm long×2 cm wide), two samples of hydrolyzed single layer inventive device (about 5 cm long×2 cm wide; about 1.5 cm long×2 cm wide), one sample of hydrolyzed two-layer inventive device (layers placed 90° from each other) (about 1.5 cm long×2 cm wide), and one sample of hydrolyzed four-layer inventive device (two layers placed 90° from the other two layer) (about 1.5 cm long×2 cm wide). Various weights were hung from the product and the resulting length was measured. For some samples, only one or two weights were measured due to sample availability. In each instance, the lowest weight (10 grams) was used for comparative purposes. The results are set forth in Table 9 below.

TABLE 9

Length Measurements of Various Products

| Material | Original length | Length with 10 g weight | Length with 20 g weight | Length with 50 g weight | Length with 200 g weight |
|---|---|---|---|---|---|
| Implantable inventive device (no hydrolysis) | 5 cm | 5 cm (1x elongation) | 5 cm (1x elongation) | 5.1 cm (~1x elongation) | 5.4 cm (~1.1x elongation) |
| Hydrolyzed inventive device | 5 cm | 25 cm (5x elongation) | 30 cm (6x elongation) | 30 cm (6x elongation) | 37.5 cm (7.5x elongation) |
| Hydrolyzed inventive device | 1.5 cm | 8.3 cm (~5.5x elongation) | — | — | — |
| Hydrolyzed inventive device with 2 layers | 1.5 cm | 3.0 cm (2x elongation) | 3.6 cm (~2.5x elongation) | — | — |
| Hydrolyzed inventive device with 4 layers | 1.5 cm | 1.8 cm (~1.2x elongation) | 2.0 cm (~1.4x elongation) | — | — |
| Hydrolyzed VYPRO ® | 1.5 cm | 2.0 cm (~1.4x elongation) | — | — | — |
| Hydrolyzed Ultrapro ® | 5 cm | 5 cm (1x elongation) | 5.5 cm (1.1x elongation) | 6.0 cm (1.2x elongation) | 6.0 cm (1.2x elongation) |
| Gynemesh | 5 cm | 5 cm (1x elongation) | 5 cm (1x elongation) | 5.1 cm (~1x elongation) | 5.4 cm (~1.1x elongation) |

A number of results can be seen from the above tests, specifically that the inventive material, in its implantable state (prior to hydrolysis) has significant strength, and is comparable to the non-absorbable polypropylene material. After hydrolysis, however, the inventive material is about 5-6 times more elastic, even when loaded with low weights (e.g., 10-20 grams). With more weight, the level of elongation is greater, as demonstrated by a 7.5x elongation with 200 grams of weight. The level of elongation after hydrolysis is greater in the inventive material than in other hydrolyzed materials, demonstrating the effectiveness and improvement of the inventive material.

What is claimed is:

1. An implantable material comprising a substantially uniform woven fabric woven from a first yarn including at least a previously kinked first non-absorbable filament and a second yarn including at least a first absorbable filament having a lower melting point than said first non-absorbable filament, wherein the substantially uniform woven fabric is randomly buckled throughout so as to exist in a random three dimensional shape, and wherein said implantable material includes a plurality of random points in three dimensional space at which said first absorbable filaments have been melted and thereby thermally bonded to the un-melted first yarn to thereby maintain said implantable material in said random three dimensional shape.

2. The implantable material according to claim 1, wherein said first or second yarn further comprises a second absorbable filament, and said first or second yarn further comprises a second non-absorbable filament.

3. The implantable material of claim 1, wherein said first non-absorbable filament is polypropylene and said first absorbable filament is polydioxanone.

4. The implantable material of claim 2, wherein said first absorbable filament is polyglactin, said second absorbable filament is polydioxanone, and said first non-absorbable filament is polypropylene.

5. The implantable material of claim 1, wherein said implantable material has a thickness of about 0.01-0.125 inches.

6. The implantable material of claim 1, wherein said first absorbable filament comprises polyglactin and said first non-absorbable filament comprises polypropylene.

7. The implantable material of claim 6, wherein said first or second yarn further comprises a second absorbable filament, and wherein said second absorbable filament is polydioxanone.

* * * * *